United States Patent
Aben et al.

(10) Patent No.: US 11,983,473 B2
(45) Date of Patent: May 14, 2024

(54) METHOD AND APPARATUS FOR QUANTITATIVE FLOW ANALYSIS

(71) Applicant: Pie Medical Imaging B.V., Maastricht (NL)

(72) Inventors: Jean-Paul Aben, Limbricht (NL); Chris Johannes Catharina Bouwman, Oirsbeek (NL); Eduardo Soudah Prieto, Valladolid (ES); Riccardo Rossi Bernecoli, L'Hospitalet de Llobregat (ES)

(73) Assignee: Pie Medical Imaging B.V., Maastricht (NL)

( * ) Notice: Subject to any disclaimer, the term of this patent is extended or adjusted under 35 U.S.C. 154(b) by 0 days.

(21) Appl. No.: 15/551,162

(22) PCT Filed: Feb. 26, 2016

(86) PCT No.: PCT/EP2016/054158
§ 371 (c)(1),
(2) Date: Aug. 15, 2017

(87) PCT Pub. No.: WO2016/135330
PCT Pub. Date: Sep. 1, 2016

(65) Prior Publication Data
US 2018/0032653 A1    Feb. 1, 2018

(30) Foreign Application Priority Data

Feb. 27, 2015    (EP) .................................. 15157039

(51) Int. Cl.
*G06F 30/28*    (2020.01)
*A61B 5/026*    (2006.01)
(Continued)

(52) U.S. Cl.
CPC .............. *G06F 30/28* (2020.01); *A61B 5/026* (2013.01); *A61B 6/032* (2013.01); *A61B 6/504* (2013.01);
(Continued)

(58) Field of Classification Search
CPC .. G06F 17/5009; G06F 30/28; G06F 2111/10; G16H 50/50; A61B 6/503;
(Continued)

(56) References Cited

U.S. PATENT DOCUMENTS 6,148,095 A * 11/2000 Prause .................... G06T 17/00
382/131
6,217,522 B1 * 4/2001 Shoshan ................ A61B 5/021
600/490
(Continued)

FOREIGN PATENT DOCUMENTS

JP    2009518097 A    5/2009
JP    2013534154 A    9/2013
(Continued)

OTHER PUBLICATIONS

Wu, Xunlei, Jérémie Allard, and Stéphane Cotin. "Real-time modeling of vascular flow for angiography simulation." International Conference on Medical Image Computing and Computer-Assisted Intervention. Springer, Berlin, Heidelberg, 2007. (Year: 2007).*
(Continued)

*Primary Examiner* — Boris Gorney
*Assistant Examiner* — David A Hopkins
(74) *Attorney, Agent, or Firm* — Gordon & Jacobson, P.C.

(57) ABSTRACT

Method for quantitative flow analysis of a tree of conduits perfusing an organ from at least two bi-dimensional images, the method comprising the following steps: a) making a 3D reconstruction of at least part of the tree from said at least (Continued)

two bi-dimensional images; b) identifying a segment of interest within the 3D reconstruction either automatically or semi-automatically upon user input; c) making calculations based on the 3D reconstruction to determine geometrical features of the conduits such as diameters, lengths, curvatures, centrelines or the like; d) receiving indication from the user to input a multi-scale functional model of the tree to be considered for the flow analysis and to input the location of the segment of interest within such model; e) adjusting the part of the functional model related to the segment of interest using geometrical features of the 3D reconstruction; f) performing quantitative flow analysis based on the functional model so obtained. A corresponding apparatus and computer program are also disclosed.

36 Claims, 14 Drawing Sheets

(51) Int. Cl.
| | |
|---|---|
| A61B 6/00 | (2006.01) |
| A61B 6/03 | (2006.01) |
| A61B 6/50 | (2024.01) |
| G06F 30/20 | (2020.01) |
| G06T 7/00 | (2017.01) |
| G16H 50/50 | (2018.01) |
| G06F 111/10 | (2020.01) |

(52) U.S. Cl.
CPC ............ *A61B 6/507* (2013.01); *A61B 6/5217* (2013.01); *G06F 30/20* (2020.01); *G06T 7/0012* (2013.01); *G16H 50/50* (2018.01); *A61B 2576/023* (2013.01); *G06F 2111/10* (2020.01); *G06T 2207/10081* (2013.01); *G06T 2207/30048* (2013.01)

(58) Field of Classification Search
CPC ....... A61B 6/504; A61B 6/507; A61B 6/5217; A61B 2576/023; G06T 2207/30048; G06T 7/0012; G06T 2207/10081
See application file for complete search history.

(56) References Cited

U.S. PATENT DOCUMENTS

| | | | | |
|---|---|---|---|---|
| 8,073,224 | B2* | 12/2011 | Strobel | A61B 6/469 |
| | | | | 382/130 |
| 9,087,147 | B1* | 7/2015 | Fonte | A61B 8/04 |
| 9,189,600 | B2* | 11/2015 | Spilker | G06V 10/40 |
| 9,202,010 | B2* | 12/2015 | Taylor | G06F 30/20 |
| 2006/0224070 | A1* | 10/2006 | Sharrock | A61B 5/02007 |
| | | | | 600/500 |
| 2008/0009698 | A1 | 1/2008 | Boese et al. | |
| 2010/0017171 | A1* | 1/2010 | Spilker | G16H 30/40 |
| | | | | 703/2 |
| 2010/0241404 | A1 | 9/2010 | Taylor | |
| 2011/0275944 | A1* | 11/2011 | Qasem | A61B 5/0225 |
| | | | | 600/493 |
| 2012/0041739 | A1* | 2/2012 | Taylor | A61B 6/504 |
| | | | | 703/11 |
| 2012/0072190 | A1* | 3/2012 | Sharma | G06T 7/0016 |
| | | | | 703/2 |
| 2013/0132054 | A1* | 5/2013 | Sharma | G16B 5/00 |
| | | | | 703/9 |
| 2013/0246034 | A1* | 9/2013 | Sharma | A61B 6/5217 |
| | | | | 703/11 |
| 2014/0024932 | A1* | 1/2014 | Sharma | A61B 6/5217 |
| | | | | 600/431 |
| 2014/0058715 | A1 | 2/2014 | Sharma et al. | |
| 2014/0249790 | A1* | 9/2014 | Spilker | G06T 7/0012 |
| | | | | 703/11 |
| 2014/0372096 | A1* | 12/2014 | Spilker | G06T 7/0012 |
| | | | | 703/11 |
| 2015/0038860 | A1* | 2/2015 | Fonte | A61B 6/507 |
| | | | | 600/505 |
| 2015/0051888 | A1 | 2/2015 | Itu et al. | |
| 2015/0374243 | A1* | 12/2015 | Itu | A61B 5/7275 |
| | | | | 703/2 |
| 2016/0196384 | A1* | 7/2016 | Mansi | G16H 50/20 |
| | | | | 600/301 |
| 2019/0083052 | A1* | 3/2019 | Homann | A61M 5/007 |

FOREIGN PATENT DOCUMENTS

| | | |
|---|---|---|
| JP | 2014079649 A | 5/2014 |
| WO | 2014111927 A1 | 7/2014 |
| WO | 2014111929 A1 | 7/2014 |

OTHER PUBLICATIONS

Nakauchi, Yoshifumi, et al. "Quantitative myocardial perfusion analysis using multi-row detector CT in acute myocardial infarction." Heart 98.7 (2012): 566-572. (Year: 2012).*
Vogelzang, Mathijs, et al. "Computer-assisted myocardial blush quantification after percutaneous coronary angioplasty for acute myocardial infarction: a substudy from the TAPAS trial." European heart journal 30.5 (2009): 594-599. (Year: 2009).*
Vasan, Ramachandran S. "Biomarkers of cardiovascular disease: molecular basis and practical considerations." Circulation 113.19 (2006): 2335-2362. (Year: 2006).*
Reymond, Philippe, et al. "Validation of a patient-specific one-dimensional model of the systemic arterial tree." American Journal of Physiology-Heart and Circulatory Physiology 301.3 (2011): H1173-H1182. (Year: 2011).*
Mynard, Jonathan P., Daniel J. Penny, and Joseph J. Smolich. "Scalability and in vivo validation of a multiscale numerical model of the left coronary circulation." American Journal of Physiology-Heart and Circulatory Physiology 306.4 (2013): H517-H528. (Year: 2013).*
Schrauwen, Jelle TC, et al. "Fast and accurate pressure-drop prediction in straightened atherosclerotic coronary arteries." Annals of biomedical engineering 43.1 (2015): 59-67. (Year: 2014).*
Ponzini, Raffaele, et al. "Reliable CFD-based estimation of flow rate in haemodynamics measures." Ultrasound in medicine & biology 32.10 (2006): 1545-1555. (Year: 2006).*
Saito, Tsuneo, et al. "Three-dimensional quantitative coronary angiography." IEEE Transactions on Biomedical Engineering 37.8 (1990): 768-777. (Year: 1990).*
Sarry, Laurent, et al. "Assessment of stenosis severity using a novel method to estimate spatial and temporal variations of blood flow velocity in biplane coronarography." Physics in Medicine & Biology 42.8 (1997): 1549. (Year: 1997).*
EP14306939.1, certied copy of filing for the PCT filing (Year: 2016).*
Huo, Yunlong, et al. "Which diameter and angle rule provides optimal flow patterns in a coronary bifurcation ?. " Journal of biomechanics 45.7 (2012): 1273-1279. (Year: 2012).*
Itzchak, Yacov, et al. "Determination of the pressure drop across an arterial stenosis utilizing angiocinedensitometry." The Yale journal of biology and medicine 50.4 (1977): 375. (Year: 1977).*
Mcdonough, James M. "Lectures in elementary fluid dynamics: physics, mathematics and applications." (2009). University of Kentucky (Year: 2009).*
Liao, Jingsheng, and John KJ Li. "Modeling of the coronary circulatory system." Cardiovascular Engineering 5.3 (2005): 141-150. (Year: 2005).*
University of Minnesota, Atlas of Human Cardiac Anatomy, Physiology Tutorial on "Blood Flow", accessed online on May 29, 2020 (Year: 2020).*
Merriam Webster dictionary, Definition of the term "cloud", accessed online on May 29, 2020 (Year: 2020).*

(56) References Cited

OTHER PUBLICATIONS

Soudah, Eduardo, et al. "A reduced-order model based on the coupled 1D-3D finite element simulations for an efficient analysis of hemodynamics problems." Computational Mechanics 54.4 (2014): 1013-1022. (Year: 2014).*
Gatzov, Plamen, et al. "Blood flow velocity in donor coronary artery depends on the degree and pattern of collateral vessel development: a study using thrombolysis in myocardial infarction frame count method." Catheterization and cardiovascular interventions 60.4 (2003): 462-468. (Year: 2003).*
Willerson, James T., and David R. Holmes Jr., eds. Coronary artery disease. Springer, 2015. Online ISBN 978-1-4471-2828-1, First Online Date: Jan. 27, 2015 (Year: 2015).*
Kim, Hyun Jin, et al. "On coupling a lumped parameter heart model and a three-dimensional finite element aorta model." Annals of biomedical engineering 37.11 (2009): 2153-2169. (Year: 2009).*
Library of Congress, STL File Format Description, Accessed on Feb. 11, 2021 (Year: 2021).*
United States National Institute of Health, National Cancer Institute, for MRI, Accessed on Feb. 12, 21 (Year: 2021).*
United States National Institute of Health, National Cancer Institute, for CT Scan, Accessed on Feb. 12, 21 (Year: 2021).*
United States Federal Drug Administration, "Computed tomography (CT)" Definition, Accessed Feb. 12, 2021 (Year: 2021).*
United States Federal Drug Administration, MRI Definition, Accessed Feb. 12, 2021 (Year: 2021).*
Pant, Sanjay, et al. "A methodological paradigm for patient-specific multi-scale CFD simulations: from clinical measurements to parameter estimates for individual analysis." International journal for numerical methods in biomedical engineering 30.12 (2014): 1614-1648. (Year: 2014).*
Zhang, Zhang, Shigeho Takarada, and Sabee Molloi. "Quantification of coronary microvascular resistance using angiographic images for volumetric blood flow measurement: in vivo validation." American Journal of Physiology-Heart and Circulatory Physiology 300.6 (2011): H2096-H2104. (Year: 2011).*
Berry, Colin, et al. "Importance of collateral circulation in coronary heart disease." European heart journal 28.3 (2007): 278-291. (Year: 2007).*
Gai, Jing-Jing, et al. "Calculation of coronary angiographic total blush in patients with coronary artery disease and its prognostic implication." Chinese medical journal 128.18 (2015): 2485. (Year: 2015).*
Henriques, Jose PS, et al. "Angiographic assessment of reperfusion in acute myocardial infarction by myocardial blush grade." Circulation 107.16 (2003): 2115-2119. (Year: 2003).*
Hofmann, Nina Patricia, et al. "Quantitative assessment of myocardial blush grade in patients with coronary artery disease and in cardiac transplant recipients." World journal of cardiology 6.10 (2014): 1108. (Year: 2014).*
Geven, Maartje CF, et al. "A physiologically representative in vitro model of the coronary circulation." Physiological measurement 25.4 (2004): 891.Geven, Maartje CF, et al. "A physiologically representative in vitro model of the coronary circulation." Physiological measurement 25.4 (2004): 891. (Year: 2004).*
Mynard, J. P., et al. "A numerical model of neonatal pulmonary atresia with intact ventricular septum and RV-dependent coronary flow." International Journal for Numerical Methods in Biomedical Engineering 26.7 (2010): 843-861. (Year: 2010).*
Sinclair, Matthew D., et al. "Measurement and modeling of coronary blood flow." Wiley Interdisciplinary Reviews: Systems Biology and Medicine 7.6 (2015): 335-356. (Year: 2015).*
Tu, Shengxian, et al. "Fractional flow reserve calculation from 3-dimensional quantitative coronary angiography and TIMI frame count: a fast computer model to quantify the functional significance of moderately obstructed coronary arteries." JACC: Cardiovascular Interventions 7.7 (2014): 768-777. (Year: 2014).*

Vogel, Rolf, et al. "Collateral-flow measurements in humans by myocardial contrast echocardiography: validation of coronary pressure-derived collateral-flow assessment." European heart journal 27.2 (2006): 157-165. (Year: 2006).*
Vijayan, Sethumadhavan, et al. "Assessing coronary blood flow physiology in the cardiac catheterisation laboratory." Current cardiology reviews 13.3 (2017): 232-243. (Year: 2017).*
Jarisch, "Myocardial Perfusion Evaluation Using Only Six Projections", 2012, accessed via URL: www(dot)researchgate(dot)net/publication/271842517_Myocardial_Perfusion_Evaluation_Using_Only_Six_Projections (Year: 2012).*
Liénard, Jean, and Regis Vaillant. "Quantitative tool for the assessment of myocardial perfusion during X-ray angiographic procedures." International Conference on Functional Imaging and Modeling of the Heart. Springer, Berlin, Heidelberg, 2009. (Year: 2009).*
Marques, Koen M., et al. "Hyperaemic microvascular resistance is not increased in viable myocardium after chronic myocardial infarction." European heart journal 28.19 (2007): 2320-2325. (Year: 2007).*
Payne, Alexander R., et al. "Bright-blood T2-weighted MRI has higher diagnostic accuracy than dark-blood short tau inversion recovery MRI for detection of acute myocardial infarction and for assessment of the ischemic area at risk and myocardial salvage." Circulation: Cardiovascular Imaging 4.3 (2011) (Year: 2011).*
Hermansen, Flemming, et al. "Measurement of myocardial blood flow with oxygen-15 labelled water: comparison of different administration protocols." European journal of nuclear medicine 25 (1998): 751-759. (Year: 1998).*
Kermain et al., "Investigation of the Blood Flow and Mitral-Septal Opposition in the Left Ventricle With the Obstructive Hyperthrophic Cardiomyopathy During Systole Using Fluid-Structure Interaction Technique." ASME International Mechanical Engineering Congress and Exposition. vol. 44267. 2010. (Year: 2010).*
Luo, Jianwen, and Elisa E. Konofagou. "Imaging of wall motion coupled with blood flow velocity in the heart and vessels in vivo: a feasibility study." Ultrasound in medicine & biology 37.6 (2011): 980-995. (Year: 2011).*
Min, James K., et al. "Noninvasive fractional flow reserve derived from coronary CT angiography: clinical data and scientific principles." Cardiovascular Imaging 8.10 (2015): 1209-1222. (Year: 2015).*
Payne, Alexander R., et al. "Microvascular resistance predicts myocardial salvage and infarct characteristics in ST-elevation myocardial infarction." Journal of the American Heart Association 1.4 (2012): e002246. (Year: 2012).*
Taylor, Charles A., and C. A. Figueroa. "Patient-specific modeling of cardiovascular mechanics." Annual review of biomedical engineering 11 (2009): 109-134. (Year: 2009).*
Sambuceti, Gianmario, et al. "Microvascular dysfunction in collateral-dependent myocardium." Journal of the American College of Cardiology 26.3 (1995): 615-623. (Year: 1995).*
Werner, Gerald S., et al. "Determinants of coronary steal in chronic total coronary occlusions: donor artery, collateral, and microvascular resistance." Journal of the American College of Cardiology 48.1 (2006): 51-58. (Year: 2006).*
Suh, Ga-Young. Hemodynamic Changes Quantified in Abdominal Aortic Aneurysms with Increasing Exercise Intensity Using Magnetic Resonance Imaging and Computational Fluid Dynamics. PhD Dissertation. Stanford University, 2011. See § 2.2.3 starting on p. 13, see § 3.2.4 starting on p. 58 (Year: 2011).*
Spilker, Ryan L., and Charles A. Taylor. "Tuning multidomain hemodynamic simulations to match physiological measurements." Annals of biomedical engineering 38 (2010): 2635-2648. See the abstract and pp. 2638-2640 (Year: 2010).*
Kim, Hyun Jin, et al. "Patient-specific modeling of blood flow and pressure in human coronary arteries." Annals of biomedical engineering 38 (2010): 3195-3209. See the abstract, fig. 1, and pp. 3197-3199 (Year: 2010).*
Young, Donald F., Neal Robert Cholvin, and Allan Charles Roth. "Pressure drop across artificially induced stenoses in the femoral arteries of dogs." Circulation research 36.6 (1975): 735-743. See the abstract and pp. 735-736 (Year: 1975).*

(56) References Cited

OTHER PUBLICATIONS

Itu, Lucian, et al. "Non-invasive hemodynamic assessment of aortic coarctation: validation with in vivo measurements." Annals of biomedical engineering 41 (2013): 669-681. See the abstract and pp. 670-673 (Year: 2013).*
Huo, Yunlong, et al. "A validated predictive model of coronary fractional flow reserve." Journal of the Royal Society Interface 9.71 (2012): 1325-1338. See the abstract and § 2.1 (Year: 2012).*
"A Novel Dedicated 3-Dimensional Quantitative Coronary Analysis Methodology of Bifurcation Lesions", Yoshinobu Onuma et al., EuroIntervention 2011; 6:1-00.
"Automatic Segmentation of 3D Micro-Ct Coronary Vascular Images", Lee et al., Medical Image Analysis, vol. 11 No. 6, pp. 630-647, 2007.
"Biomarkers of Cardiovascular Disease Molecular Basis and Practical Considerations", VASAN, Circulation 2006, 113:2335-2362.
"CFD-Based Functional Imaging for Arteries: In Vitro Validation", Taymallin et al., 19eme Congres Francais de Mecanique, 2009.
"Computational Fluid Dynamics Applied to Cardiac Computed Tomography for Noninvasive Quantification of Fractional Flow Reserve", Taylor et al., Journal of the American College of Cardiology, vol. 61, No. 22, 2013.
'Computer-Assisted Myocardial Blush Quantification After Percutaneous Coronary Angioplasty for Acute Myocardial Infarction: a Substudy from the TAPAS Trial', Vogelzang et al., European Heart Journal (2009) 30, 594-599.
"Fast and Accurate Pressure-Drop Prediction in Straightened Atherosclerotic Coronary Arteries", Schrauwen et al., Annals of Biomedical Engineering, 2014.
"Image-Based Computational Fluid Dynamics Modeling in Realistic Arterial Geometries", David A. Steinman, Annals of Biomedical Engineering, vol. 30, No. 4, 2002.
'Importance of the TIMI Frame Count: Implications for Future Trials', Appelby et al., Curr Control Trials Cardiovasc Med 2000, 1:31-34.
"Lumen Diameter of Normal Human Coronary Arteries: Influence of Age, Sex, Anatomic Variation, and Left Ventricular Hypertrophy or Dilation", Dodge et al., Circulation 1992; 86: 232-246.
"Measurement of Fractional Flow Reserve to Assess the Functional Severity of Coronary-Artery Stenoses", Piljs et al., New England Journal of Medicine 1996, 334:1703-1708, Jun. 1996.
"Modelling of Pulsatory Flows in Blood Vessels", Dindorf et al., Acta of Bioengineering and Biomechanics, vol. 3, No. 2, 2001.
"Normal Range of Human Left Ventricular Volumes and Mass Using Steady State Free Precession MRI in the Radial Long Axis Orientation" Clay et al., Magn Reson Mater Phy (2006) 19: 41-45.
"Patient-Specific Modelling of Blood Flow and Pressure in Human Coronary Arteries", Kim et al, Annals of Biomedical Engineering 38, 3195-3209, 2010.
"Principles of Computational Fluid Dynamics", Wesseling, Springer Series in Computational Mathematics, 29, 2009, p. 1-4.
"Quality Open Source Mesh Generation for Cardiovascular Flow Simulations", Marchandise et al., Modeling of Physiological Flows, MS&A—Modeling, Simulation and Applications, vol. 5, 2012, pp. 395-414.
"Review of Zero-D and 1-D Models of Blood Flow in the Cardiovascular System", Shi et al., BioMedical Engineering Online 2011, 10:33.
"Robust Gradient-Based 3-D/2-D registration of CT and MR to X-ray images", Markelj et al, IEEE Trans Med Imaging 2008 27(121): 1704 -14.
"The Role of Biofluid Mechanics in the Assessment of Clinical and Pathological Observations", Siebes et al, Annals of Biomedical Engineering 38, 1216-1224, 2010.
3D Imaging of Vascular Networks for Biophysical Modeling of Perfusion Distribution Within the Heart, Wijngaard et al, Journal of Biomechanics 46 (2013) 229-239.
"Angiographic Assessment of Myocardial Reperfusion in Patients Treated with Primary Angioplasty for Acute Myocardial Infarction Myocardial Blush Grade", Arnoud et al., American Heart Association 1998.

* cited by examiner

Collateral from same coronary artery:

Collateral from other coronary artery:

Step IV: 3D reduced model using CFD

Solve formula to determine the pressure drop Δp for the stenotic vessel segment (3D reconstruction) using CFD calculations

User input: Indicate segment in 1D model representing 3D reconstruction

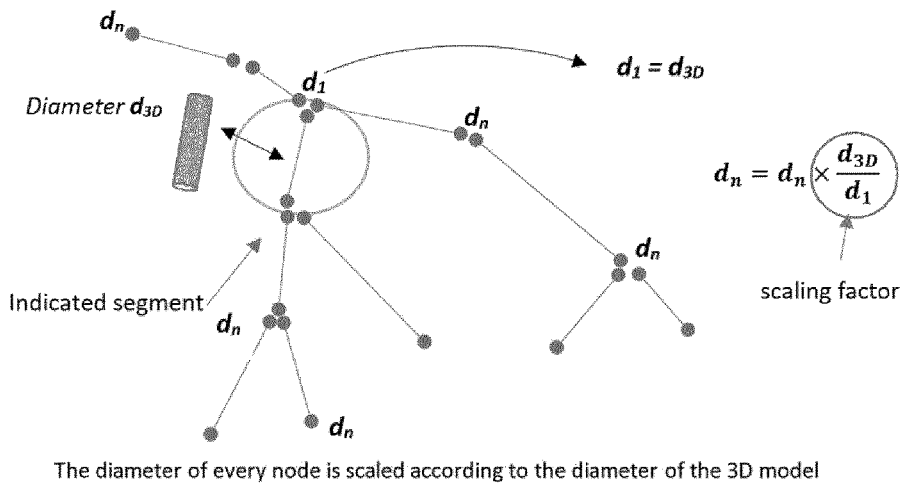

Step V: Scaling of the 1D model

$$d_n = d_n \times \left(\frac{d_{3D}}{d_1}\right)$$

scaling factor

The diameter of every node is scaled according to the diameter of the 3D model

User input: Aortic pressure
*(Determines pressure values in 1D model)*

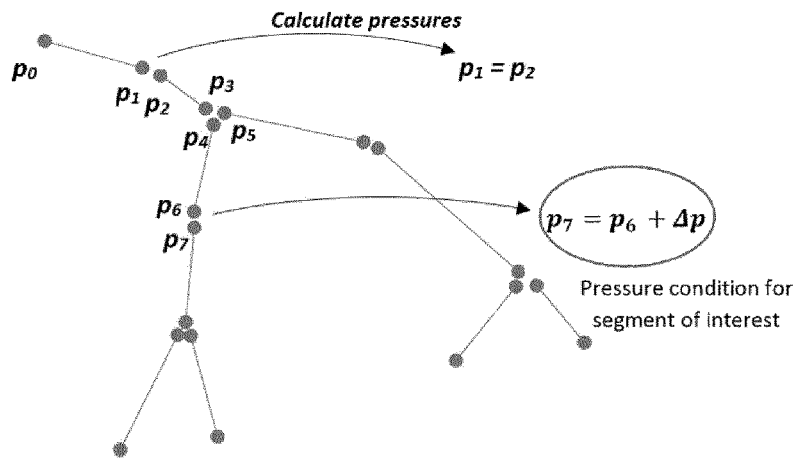

Step VI: Integration of 3D reduced model in 1D/0D model

Calculate pressures $p_1 = p_2$ $p_7 = p_6 + \Delta p$

Pressure condition for segment of interest

Fig. 11b

METHOD AND APPARATUS FOR QUANTITATIVE FLOW ANALYSIS

FIELD OF THE INVENTION

The present application relates to the technical field of medical imaging, particularly angiography imaging, although it can find application in any field where there is the need to quantify flow in obstructed or partially obstructed conduits such as in non destructive testing applications.

STATE OF THE ART

Cardiovascular disease (CVD) is one of the leading causes of deaths worldwide. CVD generally refers to conditions that involve narrowed or blocked blood vessels that can lead to reduced or absent blood and therefore oxygen supply to the sections distal to the stenosis, resulting in, for instance, chest pain (angina) and ischemia. A very important aspect in the prevention and treatment of CVD is the functional assessment of such narrowed or blocked blood vessels.

At the moment X-ray angiography is the standard technique for anatomical assessment of the coronary arteries and the diagnosis of coronary artery disease. During X-ray angiography several different two-dimensional images, also called two-dimensional projections, of the object under examination can be obtained from different views or perspectives by rotating the arm, holding the X-ray source and the image intensifier, with reference to the patient.

Although objectivity, reproducibility and accuracy in assessment of lesion severity has improved by means of quantitative coronary analysis tools, the functional significance of atherosclerotic lesions, which is the most important prognostic factor in patients with coronary artery disease, cannot be appreciated by conventional angiography which quantifies the obstruction severity based on extracted geometric features.

For intermediate coronary lesions (30%-70%), for instance, it is not always obvious if the stenosis is a risk for the patient and if it is desired to take action. Overestimation of the severity of the stenosis can cause a treatment which in hindsight would not have been necessary. Therefore exposing the patient to risks that are not necessary. Underestimation of the stenosis, however, could induce risks because the patient is left untreated when the stenosis is in reality severe. Especially for these situations it is desired to have an additional functional assessment to aid in a good decision making.

Fractional Flow Reserve (FFR) has been used increasingly over the last 10-15 years as a method to identify and effectively target the coronary lesion most likely to benefit from percutaneous coronary intervention (PCI). FFR is a technique used to measure pressure differences across a coronary artery stenosis to determine the likelihood that the stenosis impedes oxygen delivery to the heart muscle. The technique involves percutaneous inserting a pressure-transducing wire inside the coronary artery and measuring the pressure behind and before the lesion. This is best done in a hyperemic state; in the case of maximum hyperemia, blood flow to the myocardium is proportional to the myocardium perfusion pressure. FFR therefore provides a quantitative assessment of the functional severity of the coronary lesion as described in Pijls et al, "Measurement of Fractional Flow Reserve to Assess the Functional Severity of Coronary-Artery Stenoses", N Engl J Med 1996, 334:1703-1708, June 1996.

Both the ESC and ACC/AHA guidelines recommend the use of FFR in patients with intermediate coronary stenosis (30%-70%). Around 25000 FFR measurements are annually performed in the EU.

FFR, however, has some disadvantages. The technique is associated with the additional cost of a pressure wire which can be only be used once. Furthermore, measuring FFR requires invasive catheterisation with the associated cost and procedure time. Also, in order to induce (maximum) hyperemia, additional drug infusion (adenosine or papaverine) is required, which is an extra burden for the patient.

A method, that reduces costs and improves patient management, is virtual fractional flow reserve (vFFR). In vFFR, computational fluid dynamics (CFD) computations are used to estimate non-invasively the coronary blood flow circulation and derive the fractional flow reserve resulting from a coronary lesion.

One of the most difficult aspects of vFFR is the coupling of the different aspects of the computations (anatomical as well as functional) without having high computational complexity, but still incorporating as much patient specific information as needed for accurate computations.

Sophisticated numerical models have been developed that combine computational fluid dynamics (CFD) and finite element models (FEM) in order to derive patient-specific diagnostic information such as Siebes et al, "The role of biofluid mechanics in the assessment of clinical and pathological observations", Annals of Biomedical Engineering 38, 1216-1224, 2010.

One of the largest challenges is to apply realistic boundary conditions in order to simulate dynamic blood flow in the extracted geometry of the imaged vascular system.

In Taymallin et al, "CFD-based functional imaging for arteries: in vitro validation, 19eme Congres Francais de Mecanique, 2009" pressure gradients are computed using CFD in which the geometry of the aorta is extracted from MRA. Additional MR Phase contrast imaging is performed to measure the velocity which is used as boundary conditions.

In Taylor et al "Computational Fluid Dynamics Applied to Cardiac Computed Tomography for Noninvasive Quantification of Fractional Flow Reserve", Journal of the American College of Cardiology, Vol. 61, No. 22, 2013, lumped parameter models of the heart, systemic circulation and coronary microcirculation are coupled to a patient specific 3D model of the aortic root and epicardial coronary arteries extracted from CTA. Disadvantages of these approaches are that all calculations are performed exclusively in 3D. This results in a method that is of high computational complexity. Furthermore, due to the fact that these methods required MR or CT imaging, they cannot be used during the intervention in which x-ray angiography is the standard imaging modality.

In order to keep the computational demands on a feasible level a reduced model can be used in the calculation. That is, sections of the coronary tree can be represented by a one-dimensional network or zero-dimensional (lumped) model.

This multi-scale approach was adopted by Kim et al, "Patient-specific modelling of blood flow and pressure in human coronary arteries", Annals of Biomedical Engineering 38, 3195-3209, 2010 to compute physiologically realistic pressure and flow waveforms in coronary vessels at baseline conditions. 3D CFD simulations were coupled with an analytical 1D model of the circulation and a lumped-parameter model of the coronary resistance. However some underlying assumptions of these methods provide limitations as described by Wijngaard et al '3D imaging of vascular networks for biophysical modeling of perfusion distribution within the heart', Journal of Biomechanics 46 (2013) 229-239. For instance the assumption that the myocardium is healthy. Flow, for example, depends on the amount of viable myocardium and oxygen consumption. Furthermore, vascular remodelling and collateral flow are not considered, therefore the assumption is made that no collateral arteries are present which feed the coronary vessel bed distal to the lesion.

The status of the myocardium microvasculature indicates if a certain portion of the heart can be regarded to be healthy. For instance the presence of ischemia is an indication that a certain portion of the heart is not supplied with enough blood for example due to an (earlier) infarction (FIG. 1). This has an effect on the microvascular resistance and should be adjusted accordingly in the model calculations.

Furthermore, the presence of collateral flow is an adaptation of the vessels where the collateral vessels provide the heart with blood by bypassing the lesion (FIG. 2). The effect of this is that, even in the case of a very severe stenosis (for instance a total occlusion), the sections distal to the stenosis have adapted blood flow. Therefore in practice the effect of the stenosis is not necessarily severe, and not always a revascularization is the preferred treatment.

When collateral flow is present, this also has an effect on the calculations and should therefore be compensated. However, due to their size these collateral vessels are not commonly visible on X-ray angiography images and further steps are needed to determine the presence of the collateral flow based on X-ray angiography.

There is thus the need for a patient specific method that can be used during an intervention, which has low computational complexity and can cope with the status of the myocardial microvasculature and collateral flow.

SUMMARY OF THE INVENTION

It is thus an object to provide a method for quantitatively assessing a flow, particularly for quantitatively assessing the coronary blood flow from images that can be taken also during inter-operative application with a reduced procedure time and a reduced imaging related load for the patient to be able to derive the fractional flow reserve resulting from a coronary lesion.

Embodiments provide for a method, particularly a computer-implemented method, for quantitative flow analysis of a tree of conduits perfusing an organ from at least two bi-dimensional images, typically X-ray angio images taken from different perspectives, the method comprising the following steps:
a) making a 3D reconstruction of at least part of the tree from said at least two bi-dimensional images;
b) identifying a segment of interest within the 3D reconstruction either automatically or semi-automatically upon user input;
c) making calculations based on the 3D reconstruction to determine geometrical features of the conduits such as diameters, lengths, curvatures, centrelines or the like;
d) receiving indication from the user to input a multi-scale functional model of the tree to be considered for the flow analysis and to input the location of the segment of interest within such model
e) adjusting the part of the functional model related to the segment of interest using geometrical features of the 3D reconstruction;
f) performing quantitative flow analysis based on the functional model so obtained.

The input model advantageously comprises multiple segments identifying the conduits forming the tree. Such segments are associated to 1D segments in the functional model with end parts connected with lumped parameter 0D models to take the boundary conditions into account.

According to an embodiment, the method further comprises performing quantitative image analysis to correct the functional model to take into account of the status of at least parts of the conduits forming the tree performing. Such quantitative image analysis may be, for example, based on densitometric image analysis to determine the status of the perfused organ and/or the presence of collateral flows within the tree due to conduit narrowing or blockage. Geometric features extracted from the 3D reconstruction can be used as well to elaborate pressure equations of the functional model to improve computational speed.

When the teachings of the present disclosure are applied in the medical field, the tree is typically a coronary tree and the perfused organ the myocardium of the heart. In this case the input model can be chosen between a number of predetermined coronary artery dominance models comprising a left dominant, right dominant, balanced or small right/left dominant model of the coronary tree.

The status of the myocardium microvasculature can be advantageously determined through blush image analysis to correct the functional model. To reduce foreshortening and/or superimposing, the blush measurement is typically performed in at least two bi-dimensional images used to make the 3D reconstruction.

Alternatively or in combination a three-dimensional image modality such as CT can be used to register the two-dimensional images used for making the 3D reconstruction to provide a more accurate indication of the location of the myocardium upon which the blush analysis is to be performed.

As far as collateral flows in the tree are concerned, they can be determined through velocity measurements based on the bi-dimensional images. The amount of collateral flow can thus be used to correct the functional model.

According to an embodiment, the type of collateral flow can determined using densitometric image analysis and geometric information in order to correct the functional model. The collateral flow determination can be further improved using the information on the delay existing between each bi-dimensional image to increase the temporal resolution of the measurements. Biplane acquisition devices would allow to obtain this parameter easily.

According to an embodiment, the condition of the myocardium and the arterial tree vulnerability can be assessed by biomarkers. Biomarkers are biological parameters and provides specific information about the health or disease state of for instance the myocardium. These biomarkers can be obtained non-invasively by for instance blood analysis.

Densitometric, blush and/or biomarker measurements may be used to correct one or more 1D models and 0D lumped parameters models of the functional model. Further parameters can also be considered for correcting the functional model, such parameters belonging to the group consisting of: wall motion of the left ventricle, coronary motion, information on the patient such as height, weight, gender, age and blood pressure.

In case of coronary analysis, the functional model can be adjusted to simulate hyperaemia state to calculate flow, pressure and to extract the fractional flow reserve, hence there is no need for drug infusion to induce hyperemia. Also no additional imaging data is needed to perform the measurements. All the data is gathered during the procedure.

An embodiment relates to a computer product directly loadable into the memory of a computer and comprising software code portions for performing the method as disclosed above when the product is run on a computer. The computer product can also be uploaded to a cloud or high performance computing cluster to improve computation time.

Another embodiment relates to an X-ray imaging device for acquiring two-dimensional images. The device comprises a module for obtaining at least two images of a coronary tree or part of a coronary tree from different perspectives, input for receiving from a user input on a model to be considered for the flow analysis of the tree and on the location of a segment of interest within such model. The device further comprises a processing unit programmed for performing the operations of the method to calculate the fractional flow reserve in a patient.

The processing unit could be a processor or processors dedicated to perform the method according to the embodiments herein or, in a particularly advantageous configuration, the same, or part of the same, processing unit that subtends the main image acquisition functionalities of the machine thus obtaining a very compact and powerful apparatus.

A further embodiment relates to an X-ray angiography apparatus comprising an X-ray imaging device as seen above and a module for reading the information on rotational and angulation position of such imaging device for increasing accuracy of blush and densitometric measurements, particularly for improving the temporal resolution of measurements by using information on the delay between acquired image frames with respect to frontal and lateral X-ray source of the imaging device.

Further improvements will form the subject of the dependent claims.

BRIEF DESCRIPTION OF THE DRAWINGS

The characteristics of the invention and the advantages derived therefrom will be more apparent from the following description of non-limiting embodiments, illustrated in the annexed drawings.

FIGS. 11A and 11B, collectively, show a step-by-step example of an embodiment for the assessment of a stenosis in the left coronary artery;

DETAILED DESCRIPTION OF A PREFERRED EMBODIMENT

Figure 12:
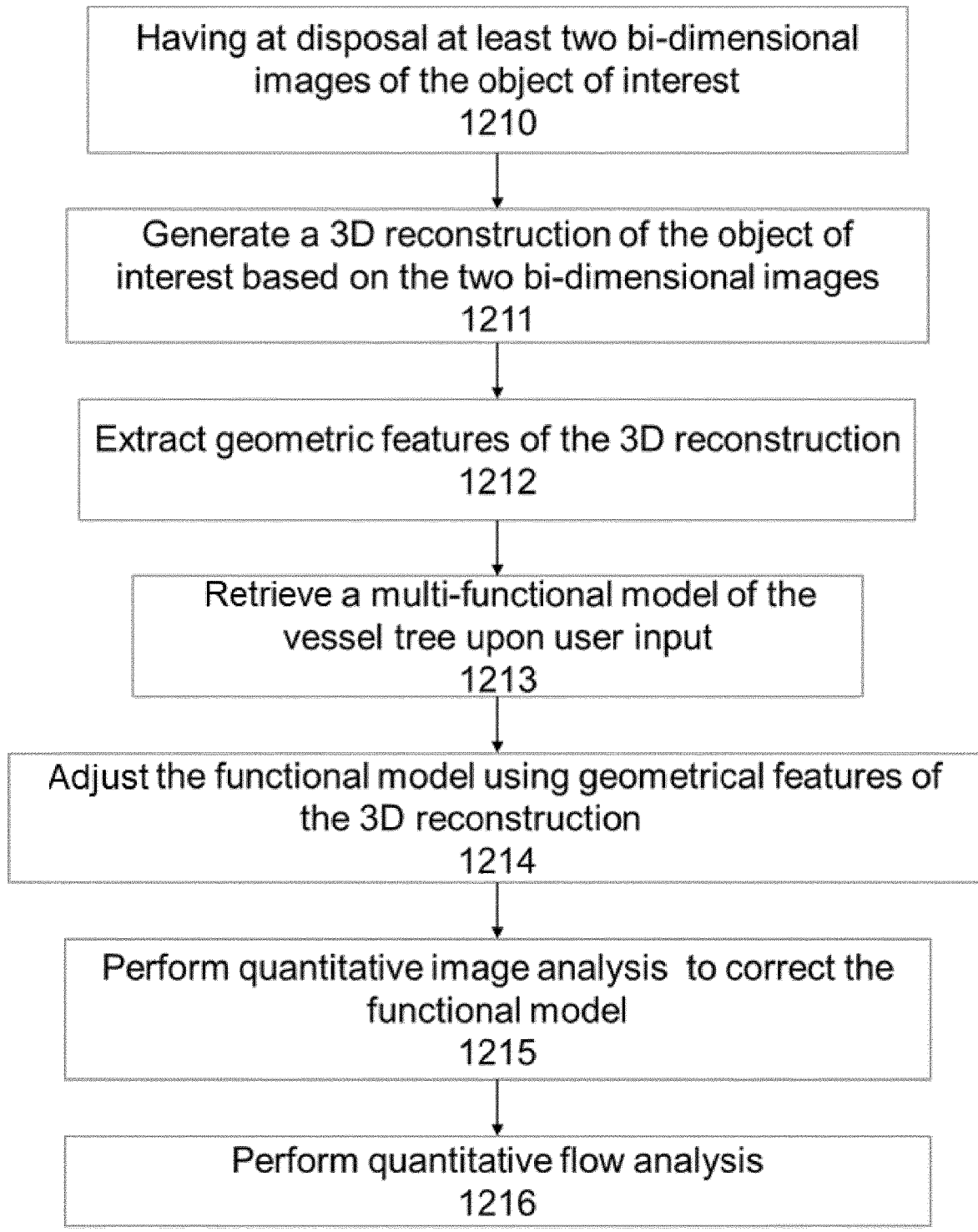
FIG. 12 shows a flow chart of a further embodiment.

FIG. 12 shows a flow chart illustrating the operations according to an embodiment of the present application. The operations employ an imaging system capable of acquiring and processing two-dimensional images of a vessel organ (or portion thereof) or other object of interest. For example a single plane or bi-plane angiographic system can be used such as those manufactured, for example, by Siemens (Artis zee Biplane) or Philips (Allura Xper FD).

Figure 14:
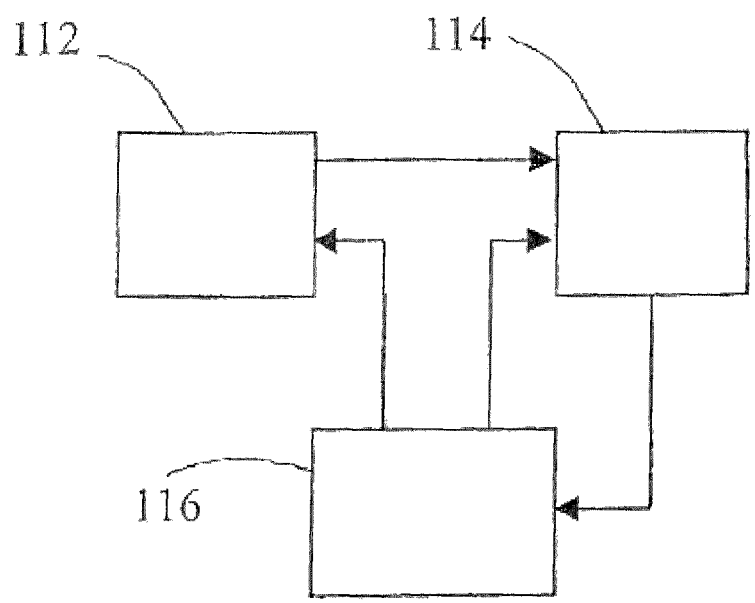
FIG. 14 shows a functional block diagram of an exemplary single plane angiographic system.

FIG. 14 is a functional block diagram of an exemplary single plane angiographic system, which includes an angiographic imaging apparatus 112 that operates under commands from user interface module 116 and will provide data to data processing module 114. The single plane angiographic imaging apparatus 112 captures a two-dimensional X-ray image of the vessel organ of interest for example in the postero-anterior (PA) direction. The single plane angiographic imaging apparatus 112 typically includes an X-ray source and detector pair mounted on an arm of a supporting gantry. The gantry provides for positioning the arm of the X-ray source and detector at various angles with respect to a patient who is supported on a table between the X-ray source and detector. The data processing module 114 may be realized by a personal computer, workstation or other computer processing system. The data processing module 114 processes the two-dimensional image captured by the single plane angiographic imaging apparatus 112 to generate data as described herein. The user interface module 116 interacts with the user and communicates with the data processing module 114. The user interface module 116 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 114 and the user interface module 116 cooperate to carry out the operations of FIG. 12 as described below.

The operations of FIG. 12 can also be carried out by software code that is embodied in a computer product (for example, an optical disc or other form of persistent memory such as a USB drive or a network server). The software code can be directly loadable into the memory of a data processing system for carrying out the operations of FIG. 12. Such data processing system can also be physically separated from the angiographic system used for acquiring the images making use of any type of data communication for getting such images as input.

In this example it is assumed that the imaging system has acquired and stored at least two two-dimensional images of an object of interest. Any image device capable of providing two-dimensional angiographic images can be used for this purpose. For example a bi-plane or single plane angiographic system can be used such as those manufactured, for example, by Siemens (Artis zee Biplane) or Philips (Allura Xper FD).

At 1210, the data processing module 114 is fed by at least two bi-dimensional images of the tree, or part of the tree, of conduits which have been obtained from different perspectives.

The data processing module at 1211 generates a 3D reconstruction using the two dimensional images. At 1212 the data processing module 114 makes calculations based on the 3D reconstruction to determine geometrical features of the conduits such as diameters, lengths, curvatures, centrelines or the like. These features are used to determine functional parameters, such as flow and pressure, in at least a segment of interest of the tree.

At 1213 the data processing module 114 retrieves from a storage unit or select from any available data source a multi-scale functional model, also called within the present description 1D/0D model, of the tree upon user input as thought for example by Kim et al, "Patient-specific modelling of blood flow and pressure in human coronary arteries". When the tree is a coronary tree and the perfused organ the myocardium of the heart, the 1D/0D model is a heart model that may be, for example, chosen between a number of predetermined models comprising a left dominant, right dominant, balanced or small right/left dominant model of the coronary tree depending on heart type.

If in the data processing model the segment of interest is identified, the part of the functional model related to the segment of interest can be adjusted at 1214 using the functional parameter derived from the geometrical features of the 3D reconstruction.

At 1215, the data processing module may perform quantitative image analysis to correct the functional model. This can, for instance, be done by taking into account the myocardium status or presence of the collateral flow. For instance the presence of ischemia is an indication that a certain portion of the heart is not supplied with enough blood for example due to an (earlier) infarction. Also the presence of collateral flow can make the stenosis less severe because the blood flow may bypass the coronary lesion in the main artery and supply enough oxygenated blood to the tissue distal to the coronary lesion.

At 1216, the processing module performs quantitative flow analysis. The vFFR value for each centreline point of the 3D reconstruction is, for example, calculated and shown on a display for the user.

Embodiments are particularly advantageous in coronary tree analysis based on two-dimensional (2D) angiographic X-ray images and they will be mainly disclosed with reference to this field, particularly for coronary arteries flow assessment, with the myocardium being the perfused organ. It is however to be understood that myocardium and arteries of the coronary tree can be substituted with any object perfused by a bed of tubular organs. FFR determination is one of the goals, although it can be appreciated that the teaching of the present disclosure can be used for determining any other flow parameter thanks to a smart flow analysis based on a 3D reconstruction coupled in a 1D/0D model of a tree of conduits in general, the coronary tree in particular.

Figure 1:
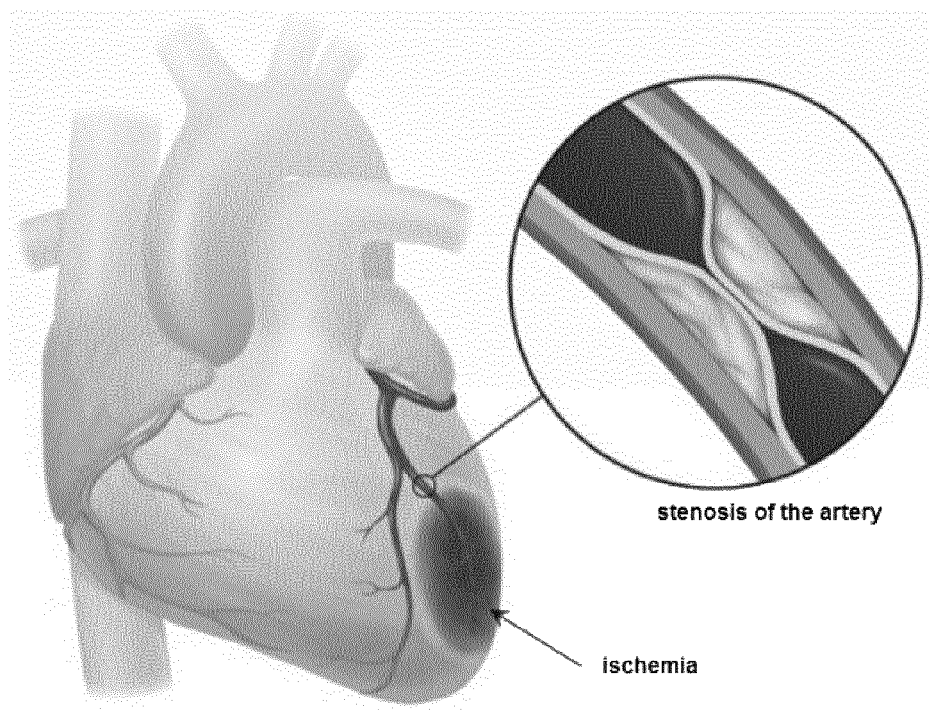
FIG. 1 shows an example of ischemia due to a stenosis of an artery.
Figure 2:
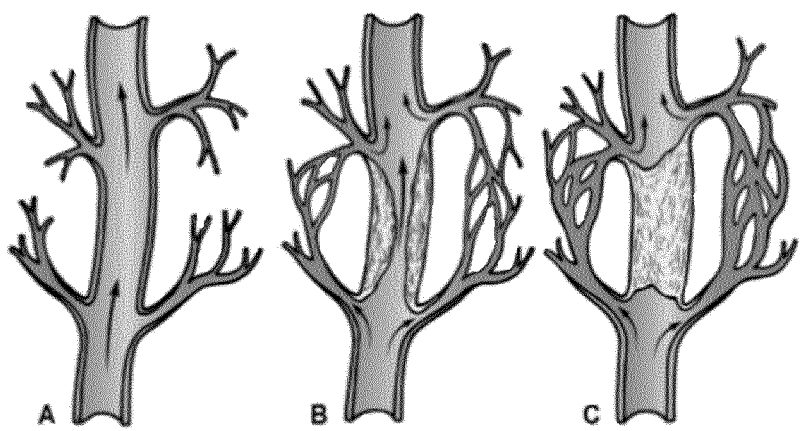
FIG. 2 shows an example of collateral flow across a lesion.
Figure 3A:
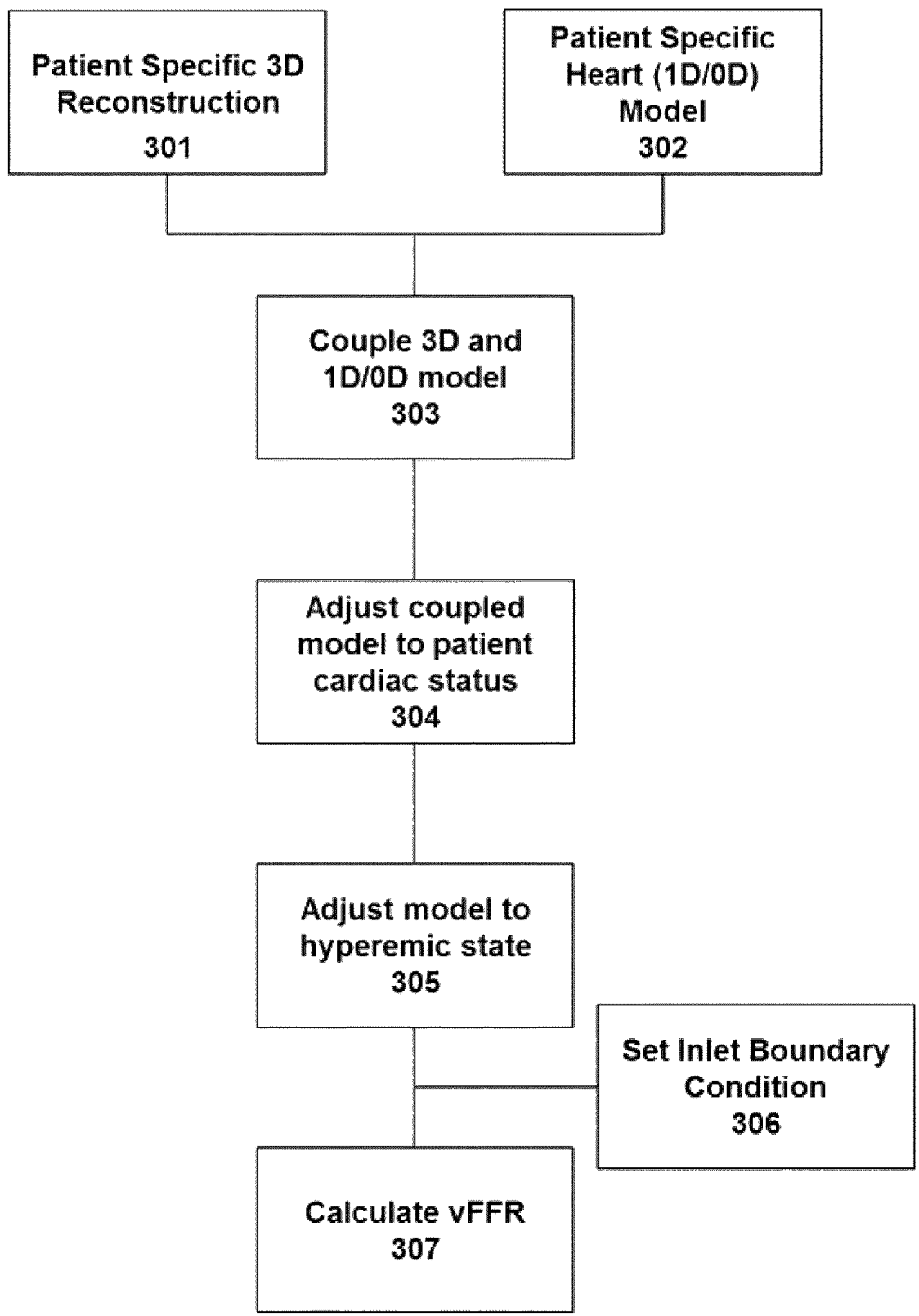
FIGS. 3A, 3B, 3C, 3D and 3E are flowcharts according to embodiments.

An embodiment is now disclosed with reference to FIG. 3A. The therein-depicted operations can, obviously, be performed in any logical sequence and can be omitted in parts. More details about the patient specific 3D reconstruction and model as shown by operation 301 in FIG. 3A is described by operations 3011 to 3014 as presented in FIG. 3B. In FIG. 3C operations 3021 and 3022 describe in more detail the patient specific multi-scale functional model (1D/0D) as described by operation 302 of FIG. 3A. For clarity, the coupling of the 3D model and 1D/0D model as depicted by operation 303 in FIG. 3A is divided in smaller operations (3031 to 3033) and they are depicted in FIG. 3D. Clarification of adjustment of the coupled model by the patient specific cardiac status as depicted in FIG. 3A by operation 304 has been given by the operations 3041 to 3044 in FIG. 3E.

Turning to FIG. 3A, in order to determine an accurate vFFR for a coronary lesion, a patient specific model is generated by the processing module 114, hereinafter also called processor. In order to get a good understanding of the coronary blood flow and pressure drop, the entire coronary tree is preferably considered. When a 3D model of the entire coronary tree is made, this has some disadvantages. First, an imaging modality is required that cannot be used during the procedure (for instance CT). Second, this approach will lead to calculations that are too time consuming and are in the order of several hours. Therefore an embodiment provides for the coronary tree to be modeled as a 1D/0D model. This simplification decreases the computational complexity significantly. The first operation of the embodiment is therefore to input/construct a patient specific 1D/0D model as shown in operation 302 of FIG. 3A.

In order to construct a patient specific 1D/0D model, at 3021 additional information specific for the patient, such as a heart type, is input from the user, particularly which type of the coronary dominant system, is applicable for the patient. A heart model, for example, depends on the heart type. The heart type is determined by the blood supply of the posterior descending artery. The posterior descending artery is supplied from blood by the right coronary artery, the left coronary artery or by both the right and left coronary artery. If e.g. the right coronary artery is the main supplier of the posterior descending artery, it is said that the patient has a right coronary dominance heart type. Likewise, a left coronary dominance heart type or balanced heart type are defined. For all heart types a specific heart model is developed. These heart models contain geometrical features (for instance diameters, vessel length and curvature) for all vessels in the coronary tree and take into account the coronary dominance. The vessel diameters, for instance, of e.g. a right coronary dominant heart model are different from the vessel diameters in a left coronary dominant heart model. The same is true for the vessel length.

At 3022, the heart type information is used by the processor to retrieve a standard 1D model to be used for this patient. The 1D model includes information on generalized diameter, length and spatial orientation of the skeleton of each segment within the coronary tree.

To improve this 1D model, the skeleton of the coronary tree (line through center of coronary arteries) may be used. For example a predefined skeleton model can be used, determined from averaged skeletons extracted from CT Angiography (CTA) image data. To make it more patient specific, predefined skeletons can be created for different heart models/types. The skeleton of the coronary tree is divided into multiple segments with specified diameter. This diameter can also be included in the predefined skeleton models as taught by Dodge et al, "Lumen diameter of normal human coronary arteries: influence of age, sex, anatomic variation, and left ventricular hypertrophy or dilation", Circulation 1992; 86: 232-246.

Furthermore the length and diameter of the segments can be determined from for example the CTA image data. Furthermore, the curvature of the arteries is taken into account by extracting the curvature per segment using for instance the skeleton of the coronary tree. If the local curvature is above a defined threshold, the segment is divided into multiple smaller segments, in this way the segment curvature is minimized and the segment's axial direction can be described by a Cartesian coordinate as expected for a 1D model. For every, subdivided segment a pressure loss reaction is defined based on the local curvature.

Next to this, the bifurcation angle between the main branch and side branches for all vessel bifurcations in the vessel tree are calculated using for instance the skeleton of the coronary tree. For every segment at a bifurcation in the vessel tree, a pressure loss is calculated taken into account the local bifurcation angle between the main vessel and side branch.

In case CTA data from the patient is available the actual skeleton, diameters, vessel length, vessel curvature and bifurcation angles can be determined to construct a patient specific 1D model. A 1D model is derived relating flow and pressure in these segments. This model can deal with wall deformation by taking into account mechanical properties of the wall and assuming axial symmetry, radial displacements and a constant pressure along each segment. This model can then be applied to each segment.

The 1D models of each of these segments are then coupled to construct one entire 1D model for the entire coronary tree taken into account pressure loss due to local curvature changes and bifurcation angles The 1D model has certain boundary conditions that apply, for example, at the end points of the vessels. Because the coronary vessels keep on branching into smaller vessels for a substantial amount, the vessel cannot be modelled in 1D entirely.

At a certain point the vessels are no longer modelled by the 1D model, but are lumped, however still containing the characteristics. This lumping is in practice a 0D model.

Figure 5:
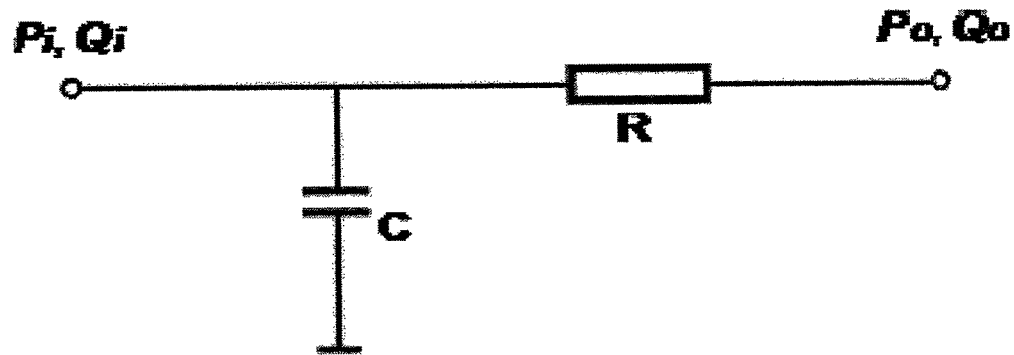
FIG. 5 shows the RC Windkessel model of the cardiovascular system.

For the lumping of the endpoints of the vessels, often the hydraulic-electrical analogue is used. The blood pressure and flow-rate can be represented by voltage and current and the effects of friction and inertia in blood flow and of vessel elasticity can be described by using resistance, inductance and capacitance respectively. By doing this, the methods for analysis of electric circuits can be applied to cardiovascular dynamics. An example of a 0D cardiovascular system analysis model is the RC Windkessel model as shown in FIG. 5 and summarized by Shi et al, "Review of Zero-D and 1-D Models of Blood Flow in the Cardiovascular System", BioMedical Engineering Online 2011, 10:33.

At the vessel ends of the coronary tree, lumped parameter models are applied. The initial values of these components can be determined using scaling laws as taught by Dindorf et al, "Modelling of pulsatory flows in blood vessels", Acts of Bioengineering and Biomechanics, Vol. 3, No. 2, 2001.

Figure 6:
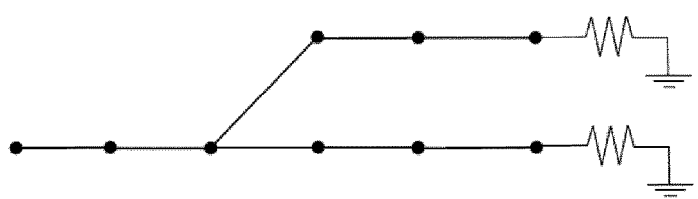
FIG. 6 shows an example of a 1D/0D model for a subset of the coronary tree.

The vessels of the coronary tree are modeled by 1D model and the vessel endpoints are lumped by 0D model, this makes a 1D/0D model. An example of a 1D/0D model for a subset of the coronary tree is shown in FIG. 6.

The heart model contains geometrical features for all vessels in the coronary tree based on the coronary dominance. These geometrical features are based on common values as described in Dodge et al, "Lumen diameter of normal human coronary arteries: influence of age, sex, anatomic variation, and left ventricular hypertrophy or dilation", Circulation 1992; 86: 232-246. Using patient specific 3D geometrical features of a segment of the coronary tree, this segment in the heart model can be set to the patient specific geometrical features instead of the common geometrical features.

Figure 3B:
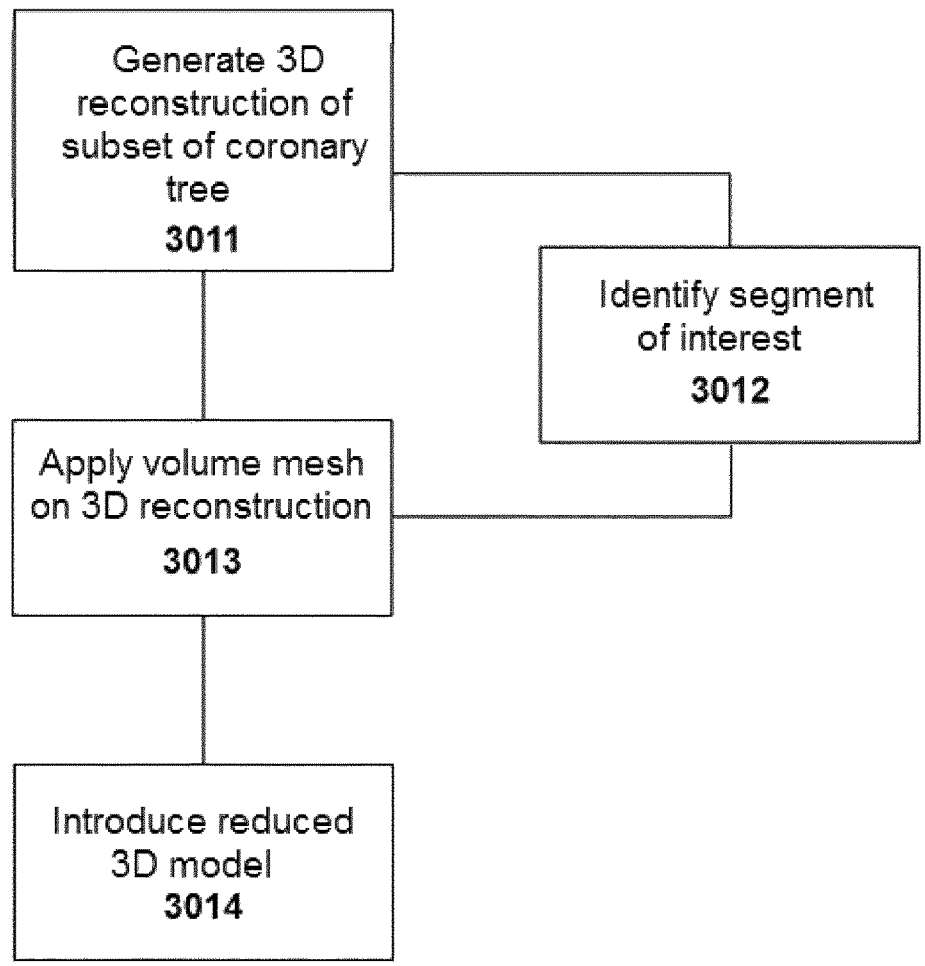
Figure 3C:
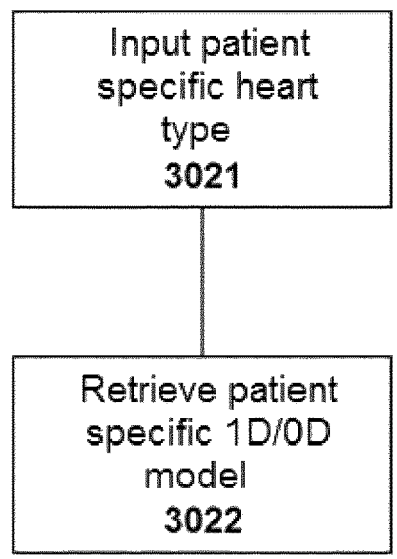
Figure 3D:
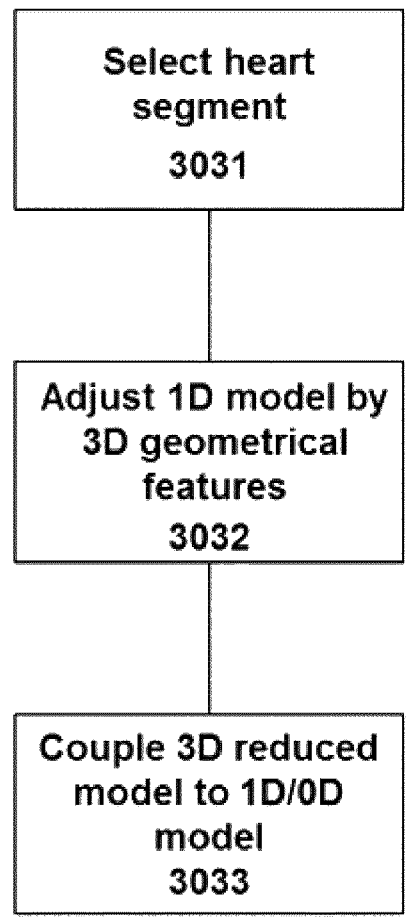
Figure 7:
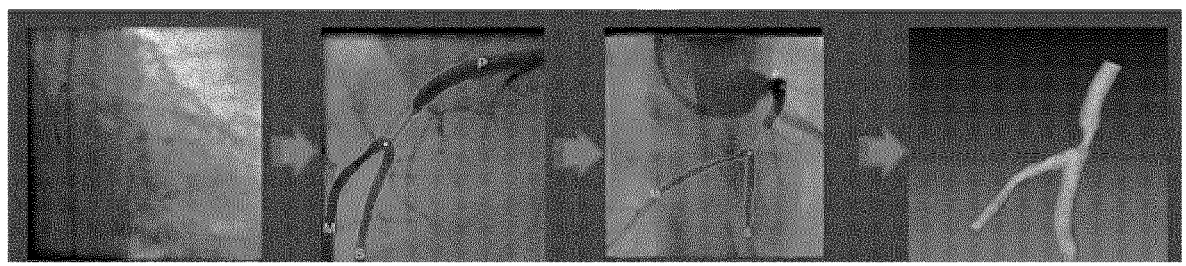
FIG. 7 schematically shows how to use two two-dimensional images to obtain a 3D reconstruction of a subset of the coronary tree.

In FIG. 3B, at 3011 the processor makes a patient specific 3D reconstruction of a subset of interest of the coronary tree which includes the coronary lesion of interest using multiple two-dimensional images as known in the art as, for instance, taught in "A novel dedicated 3-dimensional quantitative coronary analysis methodology for bifurcation lesions", Yoshinobu Onuma, Chrysafios Girasis, Jean-Paul Aben, Giovanna Sarno, Nicolo Piazza, Coen Lokkerbol, Marie-Angel Morel, Patrick W. Serruys, EuroIntervention 2011; 6:1-00. An example is shown in FIG. 7.

Figure 8:
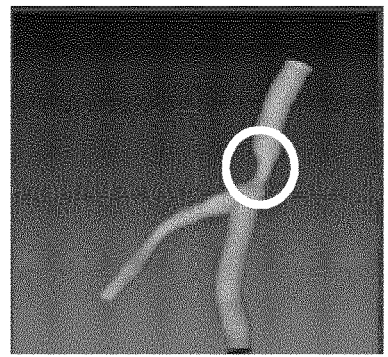
FIG. 8 schematically shows how to determine the segment of interest in the 3D reconstruction.

At 3012 in the 3D reconstruction a segment of interest is identified. This can be done manually, upon user input, or automatically or semi-automatically. This can either be done in the two-dimensional images with the processor identifying the corresponding segment in the 3D reconstruction or directly in the 3D reconstruction (as shown in FIG. 8). For example, the processor may determine a zone with a narrowing or blockage of flow and thus identify a part of the image comprising such a zone. Alternatively or in combination, a user can indicate a region of interest in the 3D reconstruction or in one or both the two-dimensional images with the processor elaborating such information to determine the position of such zone in the 3D reconstruction.

To be able to perform further CFD calculations, at 3013 a volume mesh is applied by the processor to the 3D reconstruction. To increase accuracy and computational speed of the CFD calculations element size and shape of the volume mesh can be varied throughout the vessel as taught, for instance, by Marchandise et al, "Quality open source mesh generation for cardiovascular flow simulations", Modeling of Physiological Flows, MS&A-Modeling, Simulation and Applications, Volume 5, 2012, pp 395-414. These adjustments can depend on location in the vessel (e.g. smaller elements near vessel boundaries) and geometric properties/features like local curvature and diameter/area changes.

For example in regions of the vessel with high curvature, high resolution volumetric elements are used whereas, for regions with low curvature, low resolution elements are used. This is done to minimize the amount of elements in the volume mesh.

Because it is computationally complex to insert the 3D reconstruction into the 1D/0D model, a simplification of the 3D reconstruction is advantageously made. One way of doing this is by replacing the 3D reconstruction with a reduced 3D model made as shown in operation 3014 of FIG. 3B. An advantage of this is the reduction of computation time.

Instead of using the 3D reconstruction, the 3D reconstruction is replaced by an equation that represents the pressure-flow relation. This equation is then used for further calculations. The equation can be extracted by the processor by means of CFD simulations.

CFD numerical methods and algorithms can be used to solve equations of fluid dynamics, for instance the coronary flow and pressure. These equations are based on conservation laws of classical physics (conservation of mass, momentum and energy). From these laws partial differential equations are derived and, where possible, simplified as taught by P. Wesseling, "Principles of Computational Fluid Dynamics", Springer Series in Computational Mathematics 29, 2009, p. 1-4. Simulations are used to simulate the interaction of blood with the lumen defined by boundary conditions (inlet and outlet conditions).

For these CFD simulations varying flow values can be used by the processor as a boundary condition to obtain pressure data. Optionally these calculations can be uploaded to a cloud and performed on multiple systems or uploaded to a high performance computing cluster to decrease the computation time.

Optionally, another way for reducing more computation time is to determine the pressure-flow relation based on geometric features of the 3D reconstruction as taught by Schrauwen et al, "Fast and Accurate Pressure-Drop Prediction in Straightened Atherosclerotic Coronary Arteries", Annals of Biomedical Engineering, 2014. A model can be created using features from the 3D geometry like minimum diameter, diameter changes and curvature.

The outcome of this operation performed by the processor is a fitted equation for the segment of interest that calculates a pressure drop for a given flow value.

At 303, the processor can adjust the heart model using the variation between the patient specific geometrical features and the common geometrical features in the segment of the coronary tree.

In order to make the constructed 1D/0D model more accurate and to incorporate the 3D morphology of the lesion of interest, 3D information of a segment of interest of the coronary tree can be used. This information can be obtained from two-dimensional angiographic images.

Figure 4:
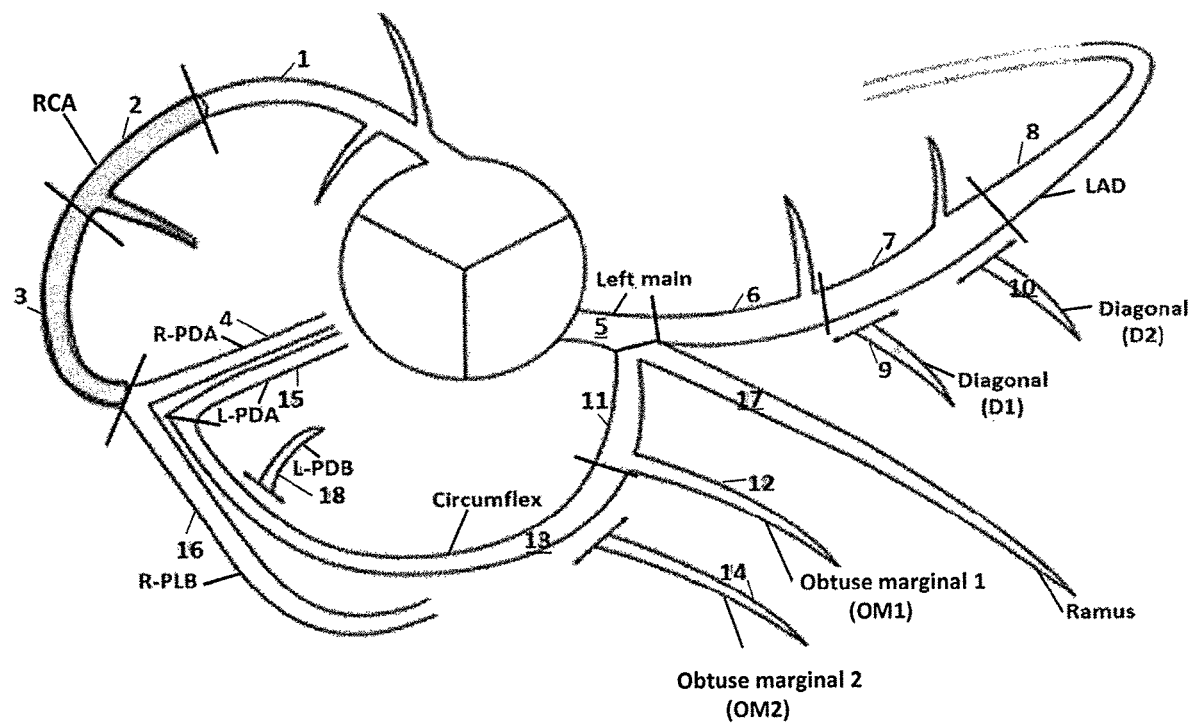
FIG. 4 shows a general model for the coronary tree according to the American Heart Association.

After simplifying the 3D reconstruction, the reduced 3D model representing the segment of interest can be inserted in the 1D/0D model. However, certain input is required to guarantee a correct coupling. First, the segment of interest as indicated earlier by the user has a certain position within the 1D/0D model. At this position, the information of the 3D reconstruction is inserted. Therefore at 3031 the processor receives an input from the user to indicate which segment(s) of the heart model (for instance the AHA model as shown in FIG. 4) is represented by the 3D reconstruction. In contrast to the 3D model, the 1D model can cope with area changes, by taking into account the elasticity of the vessel wall. An advantage of using a coupled 1D—reduced 3D model is the absence of discontinuities (for example area discontinuities) at the interfaces of the models. At the position of the segment of interest, at 3033 the processor adds the reduced 3D model to the 1D/0D model as an extra coupling condition.

Furthermore, the dimensions of the 1D/0D model are adjusted to fit the actual patient specific situation. To accomplish this, the processor performs the adjustments of the 1D/0D model to the 3D model using geometrical features extracted from the 3D reconstructed geometry. For instance at 3032 the inlet radius of the 3D reconstruction segment can be used to adjust the generalized diameters within the complete 1D model.

To make the calculations even more accurate, the 1D/0D model can be adjusted to make it even more patient specific. Different aspects can be taken into account, for instance myocardium status, the presence of collateral flow, LV wall motion, coronary motion and patient information. These aspects have not been solved previously by prior art and are of great importance for the accurate determination of the virtual fractional flow reserve in patients.

Figure 3E:
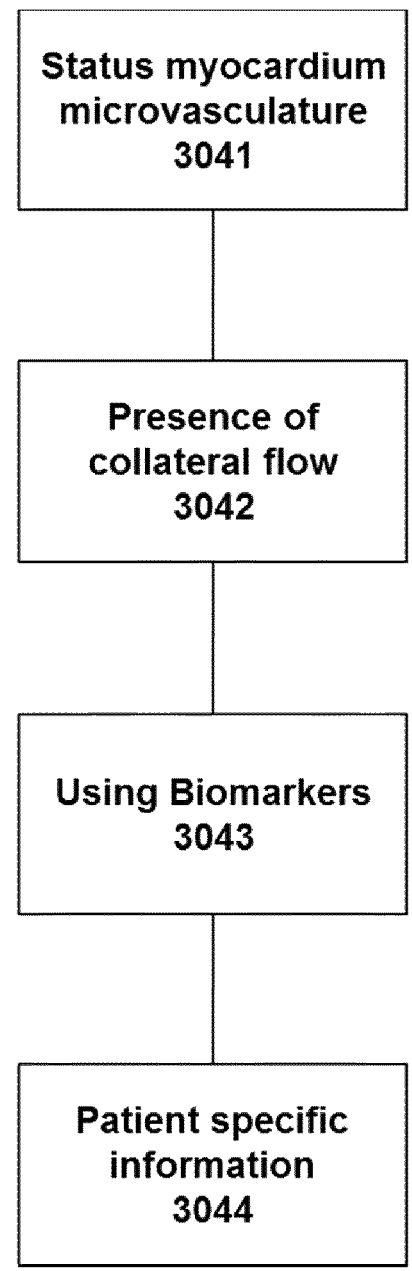

In order to improve the calculations, it is important to know the status of the myocardium microvasculature as indicated by operation 3041 of FIG. 3E. As the status of the myocardium microvasculature indicates if a certain portion of the heart can be regarded to be healthy, the status has an effect on the microvascular resistance and should be adjusted accordingly in the model calculations.

For instance the presence of ischemia is an indication that a certain portion of the heart is not supplied with enough blood for example due to an (earlier) infarction.

The status of the myocardium microvasculature can be determined by the processor by performing myocardial blush calculations. Myocardial blush is for instance calculated using two-dimensional angiographic images. In a frame of an angiographic image run a region of interest is defined distal to the expected infarct area. A motion correction between the frames in the image run is calculated using for instance correlation technique. The region of interest is shifted per frame according to the calculated motion offset. A background mask is composed in every frame of the image run by for instance a median filter. The average pixel intensity in the region of interest per image mask (e.g. 5 by 5 pixels) is calculated by subtracting the calculated background mask to image intensity of the original image for all images in the image run. In this way only image intensity of small sized structures are taken into account over time. In this way the myocardial blush can be quantified over time within the region of interest. The myocardial blush calculations as known in the art, as taught, for instance, by Vogelzang et al 'Computer-assisted myocardial blush quantification after percutaneous coronary angioplasty for acute myocardial infarction: a substudy from the TAPAS trial', European Heart Journal (2009) 30, 594-599. This can be done for one or multiple large or small sections of the heart.

Because the calculations are performed on two-dimensional angiographic images, the section of the heart that the user wishes to investigate suffers from foreshortening and superimposing. However in order to accurately determine the myocardium status, these effects is preferably minimized.

This can, for instance, be done by performing a 3D blush measurement. That is, by performing a blush measurement in both projection used to construct the 3D reconstruction or any other bi-dimensional projection. In each image the user indicates a region in which the measurements should be performed. Using the geometric information belonging to both image perspectives, for example rotation, angulation, magnification, an intersection region of the images can be calculated. Using this information, a distinction can be made between, for example, the posterior side or anterior side of the myocardium.

Another manner to minimize the effect of foreshortening and superimposing is by the use of a three-dimensional imaging modality such as from CT or MR.

When using CT imaging information, for example, a patient specific anatomical model of the patient's heart muscle can be made.

The CT data can be registered by the processor to the two-dimensional X-ray images that were used to create the 3D reconstruction as described in step 3011 of FIG. 3B. This can be done, for instance, by Markelj et al, "Robust Gradient-Based 3-D/2-D registration of CT and MR to X-ray images", IEEE Trans Med Imaging 2008 27(121): 1704-14.

By back projecting the information of the CT images onto the two-dimensional angiographic images, a more accurate semi 3D reconstruction can be made. This results in a more accurate indication of where the myocardium status measurement is to be performed. This information can for instance include information on rotational and angulation position of the X-ray imaging device, aiding in the effort to minimize foreshortening and superimposing.

When the myocardial blush is measured in specific regions of the heart, the results are used to adjust components of the 1D/0D model. However, when the blush is measured in a larger section of the heart, the results can be used to adjust the 1D/0D model between patients.

Figure 9:
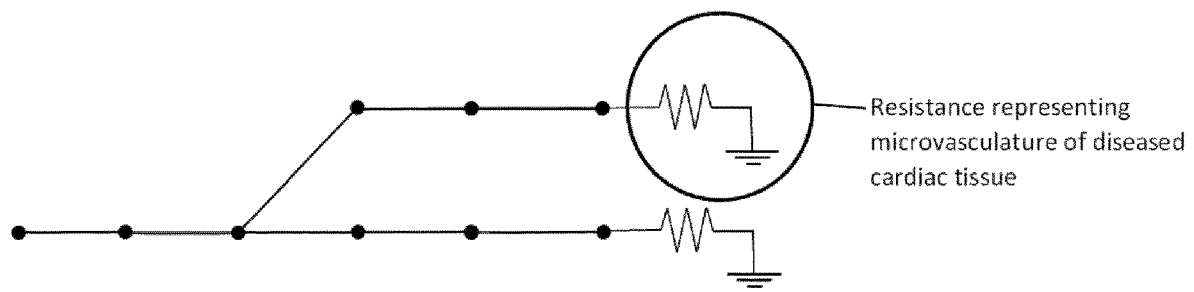
FIG. 9 shows an example of an end-resistance of the 0D model that can be adjusted using the myocardium status.

As an example of adjusting specific components of the heart model using myocardial status, at 3041 the processor adjusts end-resistances of the model as shown in FIG. 9. For example an increased microvascular resistance of a specific part of the heart is measured using blush. This can be incorporated in the model by adjusting the value of the end-resistance belonging to the coronary artery supplying that region of the heart with blood using a weighting factor.

At 3042, the processor adjusts the 1D/0D model for the presence of collateral flow. Collateral flow is an important factor for the calculations because the blood flow may bypass the coronary lesion in the main artery and supply enough oxygenated blood to the tissue distal to the coronary lesion, making the stenosis less severe. There are two types of collaterals, those across lesions and those that arise from other coronary artery/arteries. In order to obtain accurate vFFR results, the calculations have to be adjusted for the presence of collateral flow. The possible presence of collateral flow can be determined as taught in the art by Appleby et al 'Importance of the TIMI frame count: implications for future trials', Curr Control Trials Cardiovasc Med 2000, 1:31-34 and further improving this method with the use of more generic velocity information based on one or multiple angiographic images by using densitometric and geometric information.

For instance, at multiple frames from an angiographic image sequence, the propagation of the contrast along for instance a coronary artery can be determined. By defining the contrast density along the coronary artery at different frames within the angiographic image sequence, and measuring the length of the contrast density front based on densitometry information the contrast velocity can be extracted. In order to make the length measurement more accurate a 3D reconstruction of the coronary can be used. The length as determined in the 3D reconstruction is not subjected to, for example, foreshortening. Based on the local diameter and/or cross sectional area of the coronary combined with velocity information, the flow can be determined. Furthermore densitometric information from and around the coronary lesion also has a relation to the flow through that specific section of the coronary. For instance densitometric calculations can be performed just outside the coronary. If the densitometric calculations indicate that there is contrast present just outside the coronary, this indicates the presence of collateral flow. This cannot be established without densitometric information because the collaterals are too small for imaging.

When a biplane imaging system is used, such as those manufactured, for example, by Siemens (Artis zee Biplane) or Philips (Allura Xper FD), the collateral flow measurements can be made more accurate. The temporal resolution of the measurements can be improved by using the delay between each acquired frame with respect to frontal and lateral imaging source.

Figure 10:
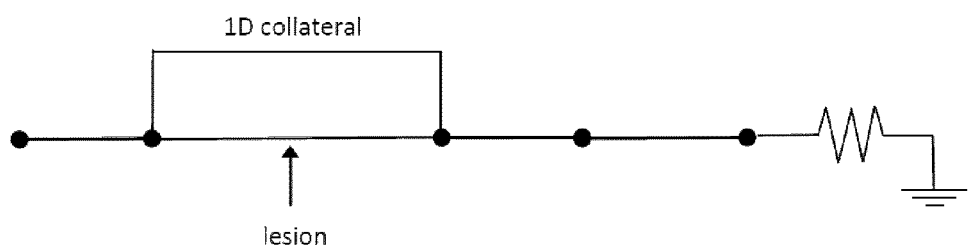
FIGS. 10A and 10B show examples of 1D collateral connection between arteries.
Figure 10:
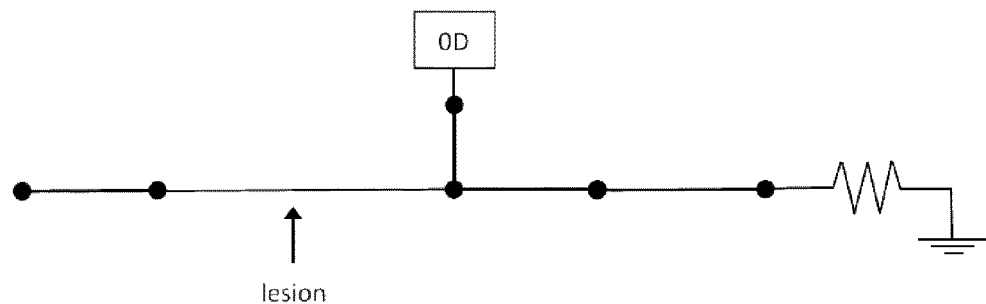

In the case of presence of collateral flow bypassing the lesion, at 3042 the processor adjusts the 1D/0D model to cope with the amount of collateral flow. In the case of collateral flow across the lesion from the same artery, the 1D model is adjusted, for example, by adding one or more elements for the collateral flow parallel to the lesion in the 1D model as illustrated in FIG. 10a.

In the case of collateral flow arising from other coronary arteries, at 3042 the processor adjusts the 1D/0D model accordingly. For example, extra 0D elements can be added simulating the collateral flow as illustrated in FIG. 10b.

Additionally, because the flow in rest state in the stenotic segment is determined, these calculations can be used to adjust the 0D parameters to adjust the 1D/0D model to patient specific measurements.

Optionally left ventricular X-ray angiogram images can be used to analyze the wall motion of the left ventricle. Using a two-dimensional image (either monoplane or biplane) of the end diastolic phase of the heart and of the end systolic phase of the heart, the wall motion of the myocardium can be determined. The wall motion provides additional information about the cardiac status regarding specific regions of the heart. Furthermore, left ventricular X-ray angiograms provides an estimation of the myocardium mass.

For example, abnormal wall motion indicates diseased heart muscle tissue having less microvascular blood flow. The end-resistance of the coupled 1D/0D model, representing this tissue with abnormal wall motion, can then be decreased accordingly.

Optionally using 4D information (3D+time) of the coronary vessels, the motion of the coronary vessels can be determined. This motion provides local information about the cardiac muscle status.

For example, coronary vessel motion deviating from normal motion can indicate diseased heart muscle tissue. Similar to the "LV wall motion" the end-resistance belonging to the part of the heart with abnormal motion can be adjusted.

A further embodiment provides for the use of patient information to improve the adjustment of the 1D/0D model parameters to make the model more patient specific as shown at 3044 of FIG. 3E. For instance patient height, weight, gender, age and heart type are used to calculate a correction factor for components of the 1D/0D models. This is done by the processor using methods well known in the art, for instance Clay et al, "Normal Range of human left ventricular volumes and mass using steady state free precession MRI in the radial long axis orientation", Magn Reson Mater Phy (2006) 19: 41-45.

Adjustment of the 1D/0D model components can be done, for instance, by adjusting 1D/0D model components between patients.

For example, tall and heavy weight patients have more cardiac mass and therefore more cardiac tissue that needs to be supplied with blood. The number of coronary arteries remains the same so there needs to be a difference in microvasculature. Therefore the end-resistance of each artery (representing the microvasculature) needs to be adopted accordingly.

Optionally, the patient specific myocardial condition and/or the myocardial arterial vulnerability is taken into account. The myocardial condition and/or myocardial arterial vulnerability can be assessed by biomarkers as shown in operation 3043 of FIG. 3E. There are numerous biological parameters, which provide clear evidence of for instance inflammation, deviating metabolic processes and pathological processes as described in Vasan et al, "Biomarkers of Cardiovascular Disease Molecular Basis and Practical Considerations", Circulation 2006, 113:2335-2362. The biological parameters can be assessed by for instance blood analysis. An example of a biomarker that can be assessed by blood analysis is troponin. Elevation of troponin levels in the blood are an indication for acute myocardial infarction and heart muscle damage due to ischemia.

Incorporating biomarkers to adjust the functional model for the condition of the myocardium and/or myocardial arteries vulnerability makes the functional model more patient specific.

All calculations discussed so far, are performed and measured under rest. However, for accurate vFFR calculations hyperemia is advantageously simulated.

At 305, the 1D/0D model is adjusted by the processor to deal with the hyperemic state. All the measurements performed for the calculations are done in rest state of the patient. Then, the 1D/0D model is adjusted accordingly and incorporating presence of collateral blood flow and myocardium vasculature status. This has as a large advantage that no hyperemic has to be induced in the patient and therefore no adenosine or papaverine needs to be administered to the patient. Adjustment of the model for hyperemia can for example be done by changing the end-resistances using scaling factors. This because in hyperemia, the demand of blood perfusion through the heart tissue increases by vasodilatation of the microvasculature. Vasodilatation can be modeled by decreasing the resistance.

Optionally information obtained from MR perfusion, CT perfusion and/or SPECT acquisitions can be used to add information regarding the myocardium microvascular flow during stress for a patient.

Because the adjustment for hyperemic state is done at this stage, all the patient specific adjustments to the 1D/0D model are also taken into account. However, if the x-ray imaging was performed during hyperemia, operation 305 can be omitted.

At 307 the processor calculates the vFFR. The 1D/0D model as described above is solved at 306 using the aortic pressure as inlet boundary condition. As a result, the vFFR value over the segment of interest is known, that is the distal pressure divided by the proximal pressure. This is known for each centerline point of the 3D reconstruction.

Figure 11A:
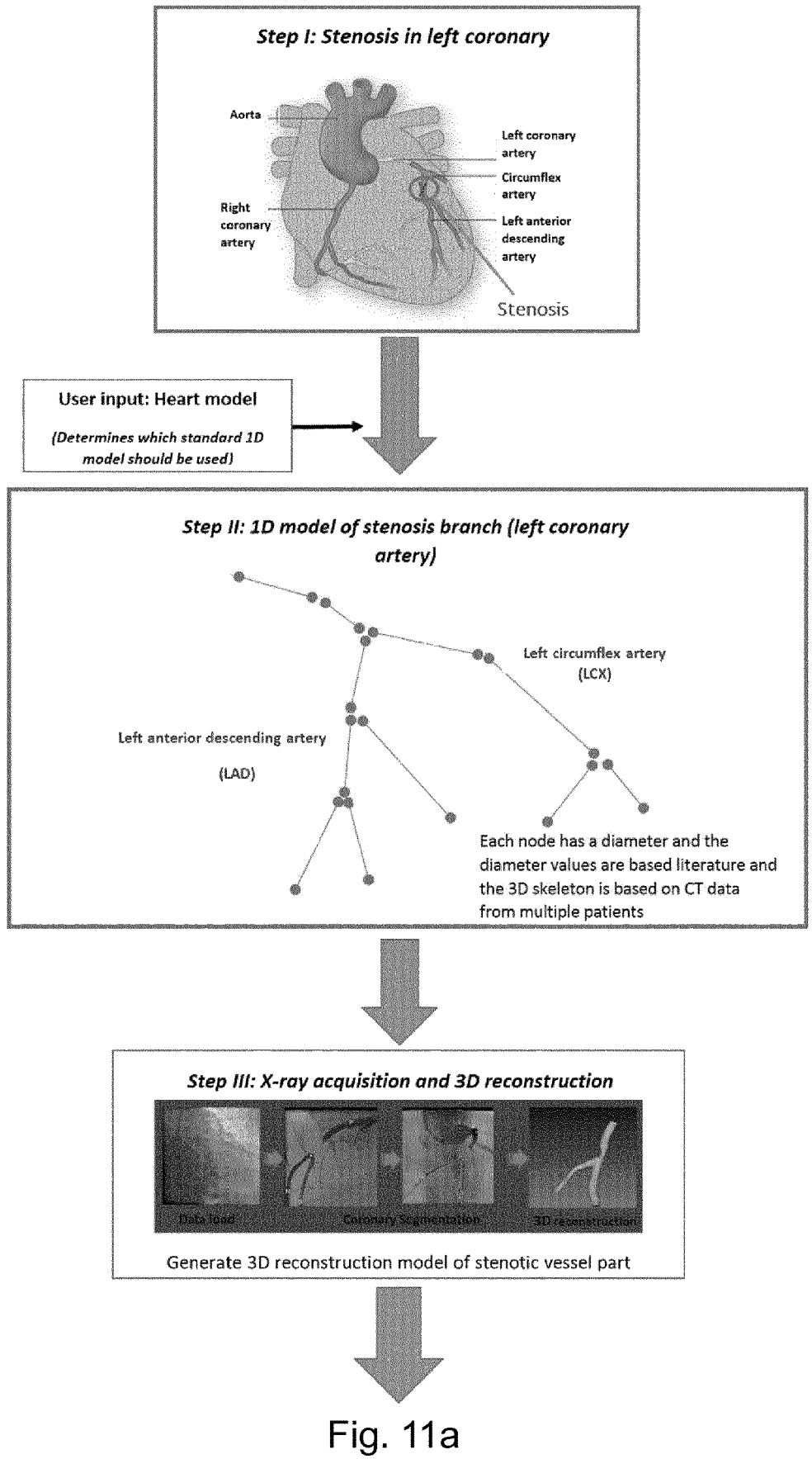

Just to make things clear, FIGS. 11A and 11B, collectively, describe an example step-by-step approach in the case of a stenosis in the left coronary artery. In this example, aortic pressure is used as input boundary condition for adjusting pressure values in the 1D model. Information on blood pressure can be rendered available from a manometer connected to a catheter or by a cuff measurement on the patient's arm.

In the present description it is made reference to a coronary tree where a stenotic artery exists, it is however to be appreciated by the skilled person that embodiments may consider also the case where several stenoses are present at different positions of the coronary tree. Each stenosis can, in fact, be calculated as a reduced 3D model to be inserted in the 1D/0D model to obtain a more accurate representation of reality.

Figure 13:
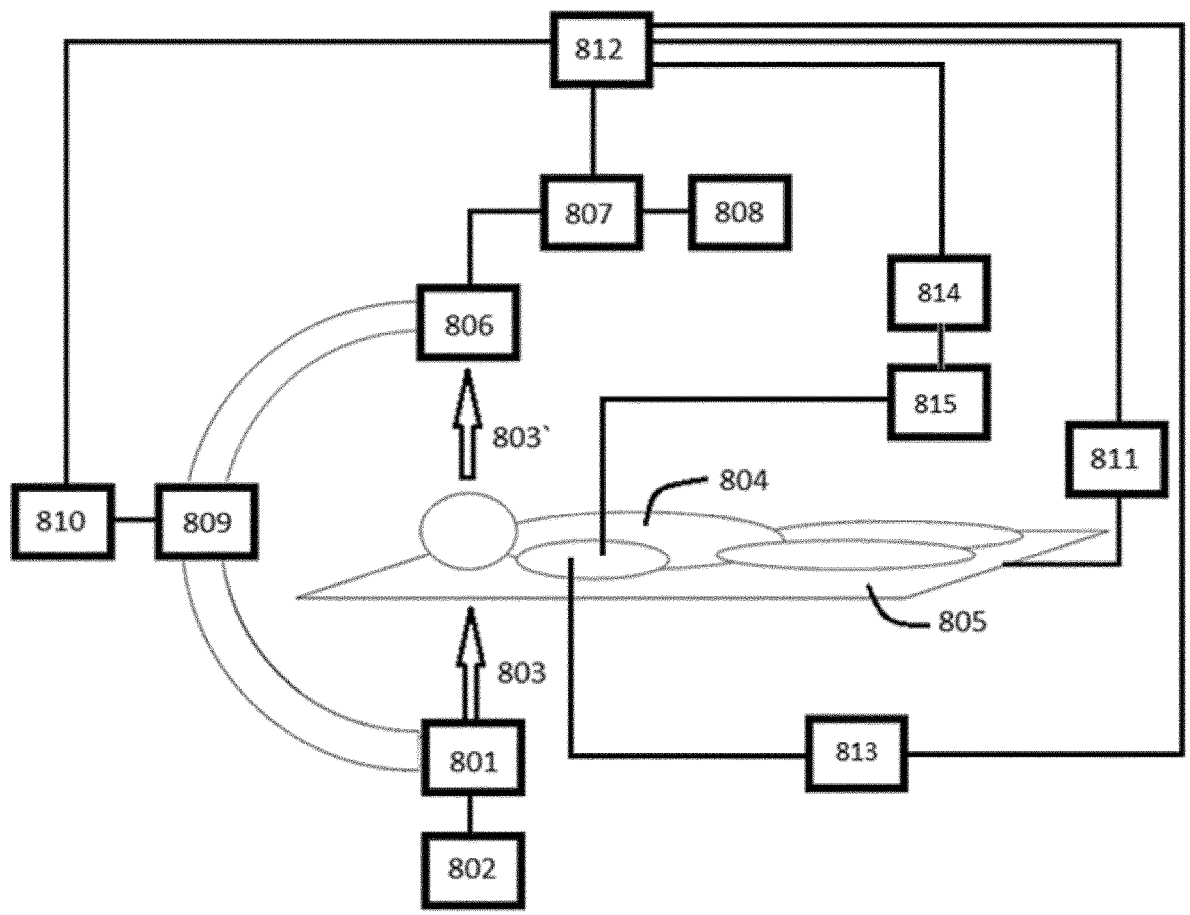
FIG. 13 shows an example of X-ray cinefluorographic unit block diagram.

Operations can be performed by processor unit on a standalone system or included directly in, for instance, an x-ray fluorographic system or any other image system to acquire two dimensional angiographic images. FIG. 13 illustrates an example of a high-level block diagram of an x-ray cinefluorograpic system. In this block diagram an example is shown on how embodiments could integrate in such a system.

Portions of the system (as defined by various functional blocks) may be implemented with dedicated hardware, analog and/or digital circuitry, and/or one or more processors operating program instructions stored in memory.

The X-ray system of FIG. 13 includes an X-ray tubes 801 with a high voltage generator 802 that generates an X-ray beam 803.

The high voltage generator 802 controls and delivers power to the X-ray tube 801. The high voltage generator 802 applies a high voltage across the vacuum gap between the cathode and the rotating anode of the X-ray tube 801.

Due to the voltage applied to the X-ray tube 801, electron transfer occurs from the cathode to the anode of the X-ray tube 801 resulting in X-ray photon-generating effect also called Bremsstrahlung. The generated photons form an X-ray beam 803 directed to the image detector 806.

An X-ray beam 803 consists of photons with a spectrum of energies that range up to a maximum determined by among others the voltage and current submitted to the X-ray tube 801.

The X-ray beam 803 then passes through the patient 804 that lies on an adjustable table 805. The X-ray photons of the X-ray beam 803 penetrate the tissue of the patient to a varying degree. Different structures in the patient 804 absorb different fractions of the radiation, modulating the beam intensity.

The modulated X-ray beam 803' that exits from the patient 804 is detected by the image detector 806 that is located opposite of the X-ray tube. This image detector 806 can either be an indirect or a direct detection system.

In case of an indirect detection system, the image detector 806 consists of a vacuum tube (the X-ray image intensifier) that converts the X-ray exit beam 803' into an amplified visible light image. This amplified visible light image is then transmitted to a visible light image receptor such as a digital video camera for image display and recording. This results in a digital image signal.

In case of a direct detection system, the image detector 806 consists of a flat panel detector. The flat panel detector directly converts the X-ray exit beam 803' into a digital image signal.

The digital image signal resulting from the image detector 806 is passed through a digital image processing unit 807. The digital image processing unit 807 converts the digital image signal from 806 into a corrected X-ray image (for instance inverted and/or contrast enhanced) in a standard image file format for instance DICOM. The corrected X-ray image can then be stored on a hard drive 808.

Furthermore the X-ray system of FIG. 13 consists of a C-arm 809. The C-arm holds the X-ray tube 801 and the image detector 806 in such a manner that the patient 804 and the adjustable table 805 lie between the X-ray tube 801 and the image detector 806. The C-arm can be moved (rotated and angulated) to a desired position to acquire a certain projection in a controlled manner using the C-arm control 810. The C-arm control allows for manual or automatic input for adjustment of the C-arm in the desired position for the X-ray recording at a certain projection.

The X-ray system of FIG. 13 can either be a single plane or a bi-plane imaging system. In case of a bi-plane imaging system, multiple C-arms 809 are present each consisting of an X-ray tube 801, an image detector 806 and a C-arm control 810.

Additionally, the adjustable table 805 can be moved using the table control 811. The adjustable table 805 can be moved along the x, y and z axis as well as tilted around a certain point.

Furthermore a measuring unit 813 is present in the X-ray system. This measuring unit contains information regarding the patient that is an input for the calculations, for instance information regarding aortic pressure, biomarkers, and/or height, length etc.

A contrast control unit that is present in the X-ray system is described in 814. Using this contrast control unit 814, the user can control the contrast injection system 815 of the patient 804 in order to inject a contrast agent into the patient 804 to be able to perform densitometric image analysis using the general processing unit 812.

A general unit 812 is also present in the X-ray system. This general unit 812 can be used to interact with the C-arm control 810, the table control 811, the digital image processing unit 807, the measuring unit 813 and the contrast control unit 814.

An embodiment is implemented by the X-ray system of FIG. 13 as follows. A clinician or other user acquires at least two X-ray angiographic images of a patient 804 by using the C-arm control 810 to move the C-arm 809 to a desired position relative to the patient 804. The patient 804 lies on the adjustable table 805 that has been moved by the user to a certain position using the table control 811.

The X-ray images are then generated using the high voltage generator 802, the X-ray tube 801, the image detector 806 and the digital image processing unit 807 as described above. These images are then stored on the hard drive 808. Using these X-ray images, the general processing unit 812 generates a 3D reconstruction, integrates a reduced model of the 3D reconstruction into a multi-functional model and adjust the functional model using geometrical features of the 3D reconstruction.

The general processing unit 812 can adjust the functional model using the information of the measuring unit 813.

Using this contrast control unit 814, the user can control the contrast injection system 815 of the patient 804 in order to inject a contrast agent into the patient 804 to be able to perform quantitative image analysis using the general processing unit 812.

The general processing unit 812 then performs quantitative flow analysis, which is displayed for the user.

There have been described and illustrated herein several embodiments of a method and apparatus for quantitative flow analysis. While particular embodiments have been described, it is not intended that the invention be limited thereto, as it is intended that the invention be as broad in scope as the art will allow and that the specification be read likewise. For example, the data processing operations can be performed offline on images stored in digital storage, such as a picture archiving and communication system (PACS) commonly used in the medical imaging arts. It will therefore be appreciated by those skilled in the art that yet other modifications could be made to the provided invention without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A computer-implemented method for quantitative flow analysis of a coronary tree perfusing a myocardium of a heart of a patient from bi-dimensional images of at least part of the coronary tree, the method comprising:
    a) generating a three-dimensional (3D) reconstruction for a subset of the coronary tree of the patient from bi-dimensional images of at least part of the coronary tree obtained from different perspectives;
    b) identifying a region of interest within the 3D reconstruction which has a narrowing or blockage of flow;
    c) generating a reduced 3D model for the region of interest from the 3D reconstruction of a), wherein the reduced 3D model for the region of interest comprises a pressure drop equation for the region of interest;
    d) generating a one-dimensional (1D) model that is specific to the patient, wherein the 1D model includes a plurality of segments representing conduits of at least part of the coronary tree of the patient, such segments including 1D segments with end parts connected with lumped parameter zero-dimensional models to take into account boundary conditions, wherein fluid flow through the segments of the 1D model is governed by a one-dimensional, axisymmetric form of fluid equations, and wherein the 1D model is based on at least one geometrical feature extracted from the 3D reconstruction of a), wherein the at least one geometrical feature is selected from a group consisting of diameter, vessel length, vessel curvature, and centerline;
    e) generating a coupled model by adding the reduced 3D model of c) to the 1D model of d) as a coupling condition at a position in the 1D model corresponding to the region of interest;
    f) updating the coupled model of e), wherein the updating is based on image analysis performed on a plurality of bi-dimensional images of at least part of the coronary tree, wherein the image analysis involves measurements of contrast propagation velocity along the coronary tree performed on at least two bi-dimensional images of the plurality of bi-dimensional images together with densiometric measurements performed on at least two bi-dimensional images of the plurality of bi-dimensional images for part of the coronary tree which has a narrowing or blockage of flow and around that part, wherein results of the measurements of contrast propagation velocity and the densiometric measurements characterize collateral flow within the coronary tree of the patient due to the narrowing or blockage of flow, and wherein results of the measurements of contrast propagation velocity and the densiometric measurements are used to adjust the coupled model of e) such that the coupled model characterizes the collateral flow within the coronary tree by adding one or more elements representing collateral flow parallel to a lesion or by adding one or more elements representing collateral flow from another coronary artery; and
    g) performing quantitative flow analysis using the coupled model updated in f).

2. The method according to claim 1, wherein the 1D model of d) is based on a standard 1D model including information on generalized diameter, length, and spatial orientation of a skeleton of segments that form the coronary tree that is adjusted based on the at least one geometrical feature extracted from the 3D reconstruction.

3. The method according to claim 1, wherein the 1D model of d) is based on a predetermined 1D model of the coronary tree selected from a left dominant model, a right dominant model, a balanced model or small right/left dominant model.

4. The method according to claim 1, wherein:
    the image analysis of f) further involves blush measurements performed on at least two bi-dimensional images of the plurality of bi-dimensional images, wherein results of the blush measurements characterize microvascular resistance of the myocardium, and wherein results of the blush measurements are used to adjust a resistance of the coupled model of e) for part of the coronary tree supplying blood to the myocardium.

5. The method according to claim 1, wherein the measurements of contrast propagation velocity are based on a delay between bi-dimensional images.

6. The method according to claim 1, wherein the updating of the coupled model in f) is based on at least one further parameter selected from a second group consisting of: wall motion of the left ventricle, coronary motion, patient information.

7. The method according to claim 1, wherein the plurality of bi-dimensional images comprise X-ray angio images.

8. The method according to claim 1, wherein the equation of the reduced 3D model is a fitted equation for the region of interest that calculates the pressure drop for a given flow value.

9. The method according to claim 1, wherein the quantitative flow analysis of g) solves the coupled model using aortic pressure as an inlet boundary condition.

10. The method according to claim 9, wherein:
the aortic pressure is derived from a cuff measurement on the patient.

11. The method according to claim 1, wherein the quantitative flow analysis of g) calculates a parameter related to pressure difference across the region of interest.

12. The method according to claim 11, wherein the parameter represents a fractional flow reserve value for the region of interest.

13. The method according to claim 12, wherein the fractional flow reserve value is calculated directly or by adjusting the coupled model to simulate hyperemia state.

14. The method according to claim 1, wherein the region of interest is identified automatically or semi-automatically based on user input.

15. The method according to claim 1, wherein the reduced 3D model for the region of interest of c) is generated using the 3D reconstruction of a) to construct a volumetric mesh for the region of interest, and using the volumetric mesh for the region of interest in conjunction with computational fluid dynamic simulations to generate the reduced 3D model for the region of interest.

16. The method according to claim 1, wherein the reduced 3D model for the region of interest of c) is generated from geometric features of the 3D reconstruction of a).

17. The method according to claim 1, wherein the lumped parameter zero-dimensional models of the 1D model of d) are based on a hydraulic-electrical analogue where a blood pressure and a flow rate is represented by a voltage and a current, respectively, and effects of friction in blood flow are represented by a resistance.

18. The method according to claim 17, wherein the hydraulic-electrical analogue further includes an inductance that represents effects of inertia in blood flow.

19. The method according to claim 17, wherein the hydraulic-electrical analogue further includes a capacitance that represents effects of vessel elasticity.

20. The method according to claim 1, wherein the image analysis of f) further involves blush measurements whose results are used to adjust a value of an end-resistance of the coupled model for the part of the coronary tree supplying blood to the myocardium.

21. The method according to claim 1, wherein the results of the measurements of contrast propagation velocity and densiometric measurements are used to adjust the coupled model by adding at least one lumped parameter zero-dimensional model that simulates the collateral flow to the coupled model.

22. The method according to claim 1, wherein the updating the coupled model of f) is further configured to update the coupled model to simulate hyperemia.

23. The method according to claim 4, wherein a three-dimensional imaging modality is used to register the at least two bi-dimensional images used for the blush measurements.

24. The method according to claim 4, wherein:
the blush measurements include subtracting a background mask from the at least two bi-dimensional images.

25. The method according to claim 4, wherein:
the blush measurements include applying motion correction to the at least two bi-dimensional images.

26. The method according to claim 4, wherein:
the blush measurements comprise a three-dimensional blush measurement involving a blush measurement performed in each of the at least two bi-dimensional images used to construct the 3D reconstruction.

27. The method according to claim 1, wherein:
the updating of f) is further based on a motion analysis of a portion of the coronary tree or the heart of the patient, wherein results of the motion analysis are used to change an element of the coupled model of e) representing an end resistance corresponding to diseased tissue.

28. The method according to claim 27, wherein:
the motion analysis involves a wall motion analysis of a left ventricle of the heart of the patient from the bidimensional images of the heart of the patient, and results of the wall motion analysis are used to change the element of the coupled model of e) representing the end resistance corresponding to the diseased tissue.

29. The method according to claim 27, wherein:
the motion analysis involves an analysis of motion of the coronary tree of the patient over time from four-dimensional information of the coronary tree of the patient, and results of the coronary tree motion analysis that deviates from normal motion are used to change the element of the coupled model of e) representing the end resistance corresponding to diseased hart tissue.

30. A non-transitory computer-readable storage medium having stored thereon executable instructions that, when executed by one or more processors of a computer system, cause the computer system to perform quantitative flow analysis of a coronary tree perfusing a myocardium of a heart of a patient from bi-dimensional images of at least part of the coronary tree, by:
 a) generating a three-dimensional (3D) reconstruction for a subset of the coronary tree of the patient from bi-dimensional images of at least part of the coronary tree obtained from different perspectives;
 b) identifying a region of interest within the 3D reconstruction which has a narrowing or blockage of flow;
 c) generating a reduced 3D model for the region of interest from the 3D reconstruction of a), wherein the reduced 3D model for the region of interest comprises a pressure drop equation for the region of interest;
 d) generating a one-dimensional (1D) model that is specific to the patient, wherein the 1D model includes a plurality of segments representing conduits of at least part of the coronary tree of the patient, such segments including 1D segments with end parts connected with lumped parameter zero-dimensional models to take into account boundary conditions, wherein fluid flow through the segments of the 1D model is governed by a one-dimensional, axisymmetric form of fluid equations, and wherein the 1D model is based on at least one geometrical feature extracted from the 3D reconstruction of a), wherein the at least one geometrical feature is selected from a group consisting of diameter, vessel length, vessel curvature, and centerline;

e) generating a coupled model by adding the reduced 3D model of c) to the 1D model of d) as a coupling condition at a position in the 1D model corresponding to the region of interest;

f) updating the coupled model of e), wherein the updating is based on image analysis performed on a plurality of bi-dimensional images of at least part of the coronary tree, wherein the image analysis involves measurements of contrast propagation velocity along the coronary tree performed on at least two bi-dimensional images of the plurality of bi-dimensional images together with densiometric measurements performed on at least two bi-dimensional images of the plurality of bi-dimensional images for part of the coronary tree which has a narrowing or blockage of flow and around that part, wherein results of the measurements of contrast propagation velocity and the densiometric measurements characterize collateral flow within the coronary tree of the patient due to the narrowing or blockage of flow, and wherein results of the measurements of contrast propagation velocity and the densiometric measurements are used to adjust the coupled model of e) such that the coupled model characterizes the collateral flow within the coronary tree by adding one or more elements representing collateral flow parallel to a lesion or by adding one or more elements representing collateral flow from another coronary artery; and g) performing quantitative flow analysis using the coupled model updated in f).

31. An X-ray imaging system comprising an imaging device for acquiring a plurality of bi-dimensional images that is operably coupled to a computer, wherein the computer is configured to a perform a method for quantitative flow analysis of a coronary tree perfusing a myocardium of a heart of a patient from bi-dimensional images of at least part of the coronary tree, the method comprising:

a) generating a three-dimensional (3D) reconstruction for a subset of the coronary tree of the patient from bi-dimensional images of at least part of the coronary tree obtained from different perspectives;

b) identifying a region of interest within the 3D reconstruction which has a narrowing or blockage of flow;

c) generating a reduced 3D model for the region of interest from the 3D reconstruction of a), wherein the reduced 3D model for the region of interest comprises a pressure drop equation for the region of interest;

d) generating a one-dimensional (1D) model that is specific to the patient, wherein the 1D model includes a plurality of segments representing conduits of at least part of the coronary tree of the patient, such segments including 1D segments with end parts connected with lumped parameter zero-dimensional models to take into account boundary conditions, wherein fluid flow through the segments of the 1D model is governed by a one-dimensional, axisymmetric form of fluid equations, and wherein the 1D model is based on at least one geometrical feature extracted from the 3D reconstruction of a), wherein the at least one geometrical feature is selected from a group consisting of diameter, vessel length, vessel curvature, and centerline;

e) generating a coupled model by adding the reduced 3D model of c) to the 1D model of d) as a coupling condition at a position in the 1D model corresponding to the region of interest;

f) updating the coupled model of e), wherein the updating is based on image analysis performed on a plurality of bi-dimensional images of at least part of the coronary tree, wherein the image analysis involves measurements of contrast propagation velocity along the coronary tree performed on at least two bi-dimensional images of the plurality of bi-dimensional images together with densiometric measurements performed on at least two bi-dimensional images of the plurality of bi-dimensional images for part of the coronary tree which has a narrowing or blockage of flow and around that part, wherein results of the measurements of contrast propagation velocity and the densiometric measurements characterize collateral flow within the coronary tree of the patient due to the narrowing or blockage of flow, and wherein results of the measurements of contrast propagation velocity and the densiometric measurements are used to adjust the coupled model of e) such that the coupled model characterizes the collateral flow within the coronary tree by adding one or more elements representing collateral flow parallel to a lesion or by adding one or more elements representing collateral flow from another coronary artery; and g) performing quantitative flow analysis using the coupled model updated in f).

32. The X-ray imaging system according to claim 31, wherein the computer is further configured to read information on a rotational and angulation position of the imaging device for use in blush and densitometric measurements, wherein said information includes information on a delay between acquired bi-dimensional image frames with respect to frontal and lateral X-ray source of the imaging device.

33. The X-ray imaging system according to claim 31, wherein the computer is embodied in a cloud computing system or high performance computing cluster.

34. The X-ray imaging system according to claim 31, further comprising an input device configured to receive user input, wherein the user input selects a predetermined 1D model to be used in the quantitative flow analysis or specifies a location of the region of interest within the 3D reconstruction.

35. A computer-implemented method for quantitative flow analysis of a coronary tree perfusing a myocardium of a heart of a patient from bi-dimensional images of at least part of the coronary tree, the method comprising:

a) generating a three-dimensional (3D) reconstruction for a subset of the coronary tree of the patient from bi-dimensional images of at least part of the coronary tree obtained from different perspectives;

b) identifying a region of interest within the 3D reconstruction which has a narrowing or blockage of flow;

c) generating a reduced 3D model for the region of interest from the 3D reconstruction of a), wherein the reduced 3D model for the region of interest comprises a pressure drop equation for the region of interest;

d) generating a one-dimensional (1D) model that is specific to the patient, wherein the 1D model includes a plurality of segments representing conduits of at least part of the coronary tree of the patient, such segments including 1D segments with end parts connected with lumped parameter zero-dimensional models to take into account boundary conditions, wherein fluid flow through the segments of the 1D model is governed by a one-dimensional, axisymmetric form of fluid equations, and wherein the 1D model is based on at least one geometrical feature extracted from the 3D reconstruction of a), wherein the at least one geometrical feature is selected from a group consisting of diameter, vessel length, vessel curvature, and centerline;

e) generating a coupled model by adding the reduced 3D model of c) to the 1D model of d) as a coupling condition at a position in the 1D model corresponding to the region of interest;

f) updating the coupled model of e), wherein the updating is based on a motion analysis of a portion of the coronary tree or heart of the patient, wherein results of the motion analysis are used to change an element of the coupled model of e) representing an end resistance corresponding to diseased tissue, wherein the motion analysis involves a wall motion analysis of a left ventricle of the heart of the patient from the bi-dimensional images of the heart of the patient, and wherein results of the wall motion analysis are used to change the element of the coupled model of e) representing the end resistance corresponding to diseased tissue; and g) performing quantitative flow analysis using the coupled model updated in f).

36. The method according to claim 35, wherein:

the motion analysis further involves an analysis of motion of the coronary tree of the patient over time from four-dimensional information of the coronary tree of the patient, and results of the coronary tree motion analysis that deviates from normal motion are used to change the element of the coupled model of e) representing the end resistance corresponding to diseased tissue.

\* \* \* \* \*